United States Patent
Satterfield et al.

(10) Patent No.: US 9,944,602 B2
(45) Date of Patent: Apr. 17, 2018

(54) PIPERIDINONE HERBICIDES

(71) Applicant: E. I. DU PONT DE NEMOURS AND COMPANY, Wilmington, DE (US)

(72) Inventors: Andrew Duncan Satterfield, Hockessin, DE (US); James Francis Bereznak, Newtown Square, PA (US); Matthew James Campbell, Rising Sun, MD (US)

(*) Notice: Subject to any disclaimer, the term of this patent is extended or adjusted under 35 U.S.C. 154(b) by 0 days.

(21) Appl. No.: 15/323,528

(22) PCT Filed: Jun. 30, 2015

(86) PCT No.: PCT/US2015/038473
§ 371 (c)(1),
(2) Date: Jan. 3, 2017

(87) PCT Pub. No.: WO2016/003997
PCT Pub. Date: Jan. 7, 2016

(65) Prior Publication Data
US 2017/0158638 A1    Jun. 8, 2017

Related U.S. Application Data

(60) Provisional application No. 62/020,140, filed on Jul. 2, 2014.

(51) Int. Cl.
| | | |
|---|---|---|
| *C07D 211/78* | (2006.01) | |
| *A01N 43/40* | (2006.01) | |
| *C07D 211/76* | (2006.01) | |
| *C07D 401/04* | (2006.01) | |
| *C07D 417/04* | (2006.01) | |

(52) U.S. Cl.
CPC ............ *C07D 211/78* (2013.01); *A01N 43/40* (2013.01); *C07D 211/76* (2013.01); *C07D 401/04* (2013.01); *C07D 417/04* (2013.01)

(58) Field of Classification Search
CPC .. C07D 211/78; C07D 211/76; C07D 401/04; C07D 417/04; A01N 43/40
See application file for complete search history.

(56) References Cited

U.S. PATENT DOCUMENTS

| | | | |
|---|---|---|---|
| 3,741,989 A | 6/1973 | Zaugg | |
| 4,594,094 A | 6/1986 | Kollmeyer | |
| 4,874,422 A | 10/1989 | Woolard | |
| 7,205,318 B2 | 4/2007 | Qiao et al. | |
| 8,293,926 B2 | 10/2012 | Yasuoka et al. | |
| 8,461,202 B2 | 6/2013 | Sancho Sanz et al. | |
| 8,575,154 B2 | 11/2013 | Kori et al. | |
| 8,946,216 B2 | 2/2015 | Deng et al. | |
| 2004/0242671 A1 | 12/2004 | Grimee et al. | |
| 2006/0019831 A1 | 1/2006 | Reinhard et al. | |
| 2007/0123508 A1 | 5/2007 | Olsson et al. | |
| 2011/0218199 A1 | 9/2011 | Georges et al. | |
| 2016/0137639 A1 | 5/2016 | Kotoku et al. | |
| 2016/0289228 A1 | 10/2016 | Defays et al. | |
| 2016/0297756 A1 | 10/2016 | Satterfield et al. | |

FOREIGN PATENT DOCUMENTS

| | | |
|---|---|---|
| CN | 102531918 B | 10/2013 |
| EP | 2336104 A1 | 6/2011 |
| IN | 1462DEL08 | 6/2008 |
| JP | 53-056288 A | 5/1978 |
| JP | 54-088114 A | 7/1979 |
| JP | 08-269145 A | 10/1996 |
| KR | 20130142477 A | 12/2013 |
| RU | 2555370 C1 | 7/2015 |
| WO | 2000/09481 A1 | 2/2000 |
| WO | 2004/046081 A1 | 6/2004 |
| WO | 2006/081562 A2 | 8/2006 |
| WO | 2009/062371 A1 | 5/2009 |
| WO | 2015/084796 A1 | 6/2015 |

(Continued)

OTHER PUBLICATIONS

XP002734980 Jan. 20, 2002, 1 page.
XP002734981 Feb. 24, 2000, 6 pages.
XP002759805 Jan. 20, 2002, 1 page.
XP002759806 Mar. 23, 2009, 1 page.
XP055297105.
XP055297107.
XP009191451.
XP002278920.
IPCOM000241978D Jun. 11, 2015, 294 pages.
XP002734980; Jan. 20, 2002.
WO0009481; Feb. 24, 2000 (XP002734981).

(Continued)

*Primary Examiner* — Johann R Richter
*Assistant Examiner* — Andriae M Holt
(74) *Attorney, Agent, or Firm* — Reed A Coats

(57) ABSTRACT

Disclosed are compounds of Formula 1, including all stereoisomers, N-oxides, and salts thereof:

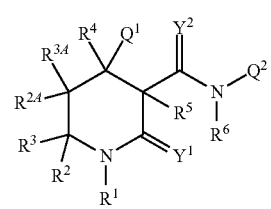

wherein $R^1$, $R^2$, $R^3$, $R^{2A}$, $R^{3A}$, $R^4$, $R^5$, $R^6$, $Q^1$, $Q^2$, $Y^1$ and $Y^2$ are as defined in the disclosure.

Also disclosed are compositions containing the compounds of Formula 1 and methods for controlling undesired vegetation comprising contacting the undesired vegetation or its environment with an effective amount of a compound or a composition of the invention.

16 Claims, No Drawings

(56) References Cited

FOREIGN PATENT DOCUMENTS

| WO | 2016/094117 A1 | 6/2016 |
| WO | 2016/164201 A1 | 10/2016 |
| WO | 2016/176082 A1 | 11/2016 |
| WO | 2016/196019 A1 | 12/2016 |
| WO | 2016/196593 A1 | 12/2016 |
| WO | 2017/023515 A1 | 2/2017 |

OTHER PUBLICATIONS

XP002759805; Jan. 20, 2002.
XP002759806; Mar. 23, 2009.
Murata et al.; "Oxidation of N-Acyl-Pyrrolidines and -Piperidines with Iron(II)-Hydrogen Peroxide and an Iron Complex-Molecular Oxygen"; *J. Chem. Soc. Perkin Trans.*; 1987; 1259-1262. (XP055297105).
Cauliez et al.; "Studies on Pyrrolidinones. On the Carbamoylation of Some Pyroglutamic Derivatives"; *J. Het. Chem.*; 33; 1996; 1233-1237. (XP055297107).
Hwang et al.; "Diastereoselective Synthesis of Oxazolidinone Derivatives and Their Antifungal Activities"; *Korean J. Of Med. Chem.*; vol. 4, No. 1; 1994; 52-56. (XP009191451).
Campaigne et el.; Synthesis of Some Ureidodihydrofurans and Related Pyrimidones as Potential Antimalarials; *J. Med. Chem.*; 1969; 339-342. (XP002278920).
IPCOM000241978D; Jun. 11, 2015.

PIPERIDINONE HERBICIDES

FIELD OF THE INVENTION

This invention relates to certain piperidinones, their N-oxides and salts, and compositions and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to a compound of Formula 1 (including all stereoisomers), including N-oxides and salts thereof, agricultural compositions containing them and their use as herbicides:

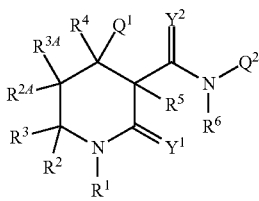

1 wherein $Q^1$ is a phenyl ring or a naphthalenyl ring system, each ring or ring system optionally substituted with up to 5 substituents independently selected from $R^7$; or a 4- to 7-membered heterocyclic ring or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members;

$Q^2$ is a phenyl ring or a naphthalenyl ring system, each ring or ring system optionally substituted with up to 5 substituents independently selected from $R^{10}$; or a 4- to 7-membered heterocyclic or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members;

$Y^1$ and $Y^2$ are each independently O, S or $NR^{12}$;

$R^1$ is H, hydroxy, amino, $C_1$-$C_6$ alkyl, cyano, formyl, $C_3$-$C_8$ alkylcarbonylalkyl, —C($C_1$-$C_4$ alkyl)=N—O($C_1$-$C_4$ alkyl), —C(O)NH$_2$, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or arylcarbonyl, arylalkenylalkyl, arylcarbonylalkyl or —CPh=N—O($C_1$-$C_4$ alkyl), each optionally substituted on ring members with up to 5 substituents independently selected from $R^{13}$; or $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^{2A}$ and $R^{3A}$ are each independently H, halogen, hydroxy, $C_1$-$C_4$ alkyl, $C_1$-$C_4$ haloalkyl or $C_1$-$C_4$ alkoxy; or $R^{2A}$ and $R^{3A}$ are taken together with the carbon atom to which they are bonded to form a $C_3$-$C_7$ cycloalkyl ring or C=O;

$R^4$ and $R^5$ are each independently H, halogen, hydroxy, $C_1$-$C_4$ alkoxy, $C_1$-$C_4$ haloalkyl or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

$R^6$ and $Q^2$ are taken together with the nitrogen atom to which they are bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members;

each $R^7$ and $R^{10}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_3$-$C_8$ alkoxyalkoxyalkyl, $C_2$-$C_8$ haloalkoxyhaloalkoxy, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or $G^2$;

each $R^8$ is independently H, cyano, $C_2$-$C_3$ alkylcarbonyl or $C_2$-$C_3$ haloalkylcarbonyl;

each $R^9$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl, $C_2$-$C_6$ haloalkylcarbonyl, —(C=O)CH$_3$ or —(C=O)CF$_3$;

each $G^1$ is independently phenyl, phenylmethyl (i.e. benzyl), pyridinylmethyl, phenylcarbonyl (i.e. benzoyl), phenoxy, phenylethynyl, phenylsulfonyl, p-methoxybenzyl or a 5- or 6-membered heteroaromatic ring, each optionally substituted on ring members with up to 5 substituents independently selected from $R^{13}$;

each $G^2$ is independently phenyl, phenylmethyl (i.e. benzyl), pyridinylmethyl, phenylcarbonyl (i.e. benzoyl), phenoxy, phenylethynyl, phenylsulfonyl or a 5- or 6-membered heteroaromatic ring, each optionally substituted on ring members with up to 5 substituents independently selected from $R^{14}$;

each $R^{13}$ and $R^{14}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl; and each u and v are independently 0, 1 or 2 in each instance of $S(=O)_u(=NR^8)_v$, provided that the sum of u and v is 0, 1 or 2.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents, the composition optionally further comprising at least one additional active ingredient selected from the group consisting of other herbicides and herbicide safeners. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "C=O" is carbonyl in the context of $R^{2,4}$ and $R^{3,4}$ are taken together with the carbon atom to which they are bonded to form a $C_3$-$C_7$ cycloalkyl ring or C=O.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxycarbonyl" denotes alkoxy substitution on carbonyl. Examples of "alkoxycarbonyl" include $CH3OC(=O)$, $CH_3CH_2OC(=O)$ and $CH_3CH_2CH_2CH_2OC(=O)$. "Alkoxyalkoxyalkyl" denotes at least alkoxy substitution on the alkoxy moiety of alkoxyalkyl moiety. Examples of "alkoxyalkoxyalkyl" include $CH_3OCH_2OCH_2$, $CH_3CH_2O(CH_3)CHOCH_2$ and $(CH_3O)_2CHOCH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$—, $CH_3CH_2S(=O)$—, $CH_3CH_2CH_2S(=O)$—, $(CH_3)_2CHS(=O)$— and the different butylsulfinyl, pentylsulfinyl and hexylsulfinyl isomers. Examples of "alkyl sulfonyl" include $CH_3S(=O)_2$—, $CH_3CH_2S(=O)_2$-, $CH_3CH_2CH_2S(=O)_2$-, $(CH_3)_2CHS(=O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinylalkyl" denotes alkylsulfinyl substitution on alkyl. Examples of "alkylsulfinylalkyl" include $CH_3S(=O)CH_2$, $CH_3S(=O)CH_2CH_2$, $CH_3CH_2S(=O)CH_2$ and $CH_3CH_2S(=O)CH_2CH_2$. "Alkylsulfonylalkyl" denotes alkylsulfinyl substitution on alkyl. Examples of "alkylsulfinylalkyl" include $CH_3S(=O)_2CH_2$, $CH_3S(=O)_2CH_2CH_2$, $CH_3CH_2S(=O)_2CH_2$ and $CH_3CH_2S(=O)_2CH_2CH_2$. "Alkylamino", "dialkylamino", and the like, are defined analogously to the above examples. Examples of "alkylaminoalkyl" include $CH_3NHCH_2$—, $(CH_3)_2CHNHCH_2$— and $CH_3NHCH(CH_3)$—. Examples of "dialkylaminoalkyl" include $(CH_3)_2NCH_2$—, $(CH_3)_2NC(CH_3)H$— and $(CH_3)(CH_3)NCH_2$—. Examples of "dialkylaminocarbonyl" include $(CH_3)_2NC(=O)$—. Examples of "dialkylaminosulfonyl" include $(CH_3)_2NS(=O)_2$—. The term "alkoxycarbonylamino" denotes a straight-chain or branched alkoxy moieties bonded to a C(=O) moiety of carbonylamino group. Examples of "alkoxycarbonylamino" include $CH_3OC(=O)NH$— and $CH_3CH_2OC(=O)NH$—.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, 1-ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" denotes a cycloalkyl moiety linked through an oxygen atom. "Cycloalkylamino" denotes cycloalkyl substitution on an amino group. Examples of "cycloalkylalkoxy" include cyclopropylmethoxy, cyclopentylethoxy, and other cycloalkyl moieties bonded to straight-chain or branched alkoxy groups. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "halocycloalkyl", "haloalkoxy", "haloalkylthio", "haloalkenyl", "haloalkynyl", "haloalkenyloxy", "haloalkylcarbonylamino", "haloalkylsulfonylamino", "haloalkylsulfonyloxy", "haloalkoxyalkyl", "haloalkylcarbonyloxy", "haloalkylaminoalkyl" and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkylsulfinyl" include $CF_3S(=O)-$, $CCl_3S(=O)-$, $CF_3CH_2S(=O)-$ and $CF_3CF_2S(=O)-$. Examples of "haloalkylsulfonyl" include $CF_3S(=O)_2-$, $CCl_3S(=O)_2-$, $CF_3CH_2S(=O)_2-$ and $CF_3CF_2S(=O)_2-$. Examples of "haloalkenyl" include $(Cl)_2C=CHCH_2$ and $CF_3CH_2CH=CHCH_2$. Examples of "haloalkenyloxy" include $(Cl)_2C=CHCH_2O-$ and $CF_3CH_2CH=CHCH_2O-$. Examples of "haloalkynyl" include $HC\equiv CCHCl-$, $CF_3C\equiv C-$, $CCl_3C\equiv C-$ and $FCH_2C\equiv CCH_2-$. Examples of "haloalkoxyalkyl" include $CF_3OCH_2$, $ClCH_2CH_2OCH_2CH_2$, $Cl_3CCH_2OCH_2$ as well as branched alkyl derivatives. Examples of "haloalkoxycarbonyl" include $CF_3OC(=O)-$, $ClCH_2CH_2OCH_2CH_2-$, $Cl_3CCH_2OCH_2OC(=O)-$ as well as branched alkyl derivatives.

"Alkylcarbonyl" denotes a straight-chain or branched alkyl moieties bonded to a $C(=O)$ moiety. Examples of "alkylcarbonyl" include $CH_3C(=O)-$, $CH_3CH_2CH_2C(=O)-$ and $(CH_3)_2CHC(=O)-$. Examples of "alkoxycarbonyl" include $CH_3OC(=O)-$, $CH_3CH_2OC(=O)-$, $CH_3CH_2CH_2OC(=O)-$, $(CH_3)_2CHOC(=O)-$ and the different butoxy- or pentoxycarbonyl isomers. "Cycloalkylalkoxycarbonyl" denotes a cycloalkylalkyl moieties bonded to an oxygen atom of alkoxycarbonyl moiety. Examples of "cycloalkylalkoxycarbonyl" include cyclopropyl-$CH_2OC(=O)-$, cyclopropyl-$CH(CH_3)OC(=O)-$ and cyclopentyl-$CH_2OC(=O)-$.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates $CH_3OCH_2-$; $C_3$ alkoxyalkyl designates, for example, $CH_3CH(OCH_3)-$, $CH_3OCH_2CH_2-$ or $CH_3CH_2OCH_2-$; and $C_4$ alkoxyalkyl designates the various isomers of an alkyl group substituted with an alkoxy group containing a total of four carbon atoms, examples including $CH_3CH_2CH_2OCH_2-$ and $CH_3CH_2OCH_2CH_2-$.

When a compound is substituted with a substituent bearing a subscript that indicates the number of said substituents can exceed 1, said substituents (when they exceed 1) are independently selected from the group of defined substituents, (e.g., $[(R^7)_n]$, n is 1, 2, 3, 4 or 5). Further, when the subscript indicates a range, e.g. $(R)_{i-j}$, then the number of substituents may be selected from the integers between i and j inclusive. When a group contains a substituent which can be hydrogen, for example $R^1$ or $R^2$, then when this substituent is taken as hydrogen, it is recognized that this is equivalent to said group being unsubstituted. When a variable group is shown to be optionally attached to a position, for example $[R^{(7)}{}_n]$ wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no $C=C=C$, $N=C=C$, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula 1 (e.g., substituent $Q^1$) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. A "bridged bicyclic ring system" is formed by bonding a segment of one or more atoms to nonadjacent ring members of a ring. The term "ring member" refers to an atom or other moiety (e.g., $C(=O)$, $C(=S)$, $S(O)$ or $S(O)_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that $(4n+2)$ $\pi$ electrons, where n is a positive integer, are associated with the ring to comply with Hückel's rule. The term "aromatic ring or ring system" denotes a carbocyclic or heterocyclic ring or ring system in which the ring or at least one ring of the ring system is aromatic. The term "aromatic ring or ring system" is also referred to as "aryl". The term "aryl" which contains 5 to 12 ring members can be used alone or in compound words such as "arylcarbonyl". "Arylcarbonyl" denotes an aryl group bonded to a $C(=O)$ moiety. The terms "arylalkenylalkyl" and "arylcarbonylalkyl" are defined in a similar way. "Aryl" The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When $Q^1$ or $Q^2$ is 5- or 6-membered nitrogen-containing heterocyclic ring, it may be attached to the remainder of Formula 1 though any available carbon or nitrogen ring atom, unless otherwise described. As noted above, $Q^1$ and $Q^2$ can be (among others) phenyl optionally substituted with one or more substituents selected from a group of substituents as defined in the Summary of the Invention. An example of phenyl optionally substituted with zero to five substituents is the ring illustrated as U-1 in Exhibit 1, wherein, for example, $R^v$ is $R^7$ as defined in the Summary of the Invention for $Q^1$, or $R^v$ is $R^{10}$ as defined in the Summary of the Invention for $Q^2$, and r is an integer (from 0 to 5).

As noted above, $Q^1$ and $Q^2$ can be (among others) a 5- or 6-membered fully unsaturated heterocyclic ring, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for $Q^1$ and $Q^2$, and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

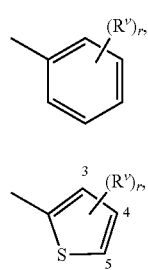

U-1

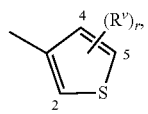

U-2

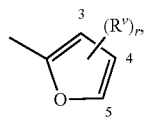

U-3

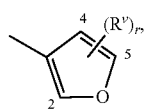

U-4

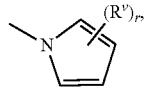

U-5

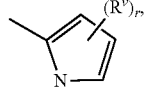

U-6

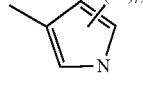

U-7

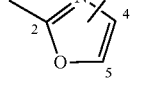

U-8

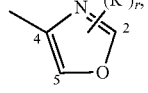

U-9

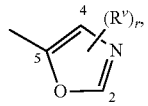

U-10

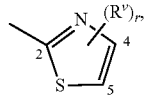

U-11

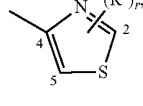

U-12

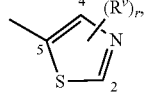

U-13

U-14

U-15

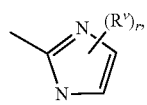 U-16
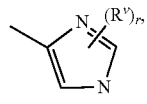 U-17
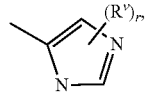 U-18
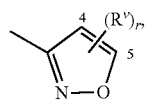 U-19
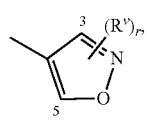 U-20
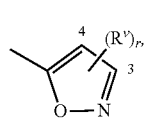 U-21
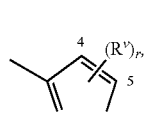 U-22
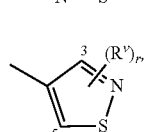 U-23
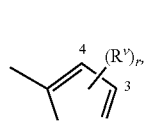 U-24
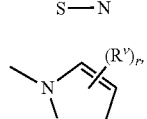 U-25
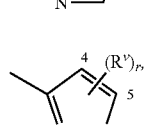 U-26
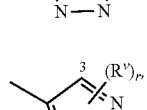 U-27
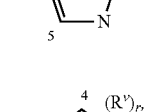 U-28
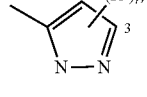
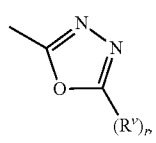 U-29
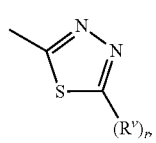 U-30
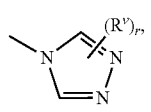 U-31
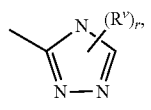 U-32
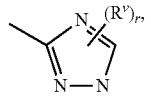 U-33
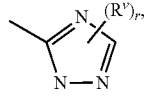 U-34
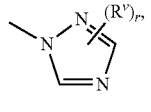 U-35
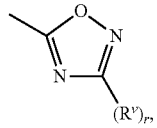 U-36
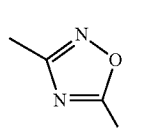 U-37
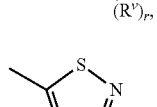 U-38
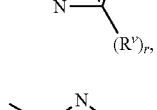 U-39
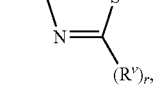 U-40
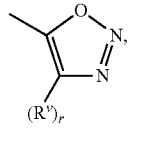

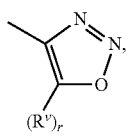
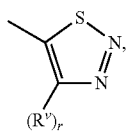
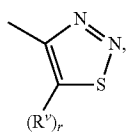
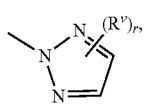
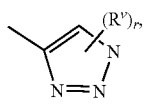
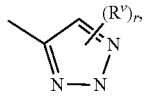
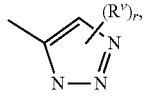
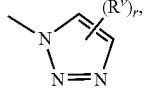
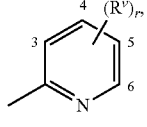
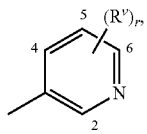
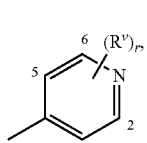
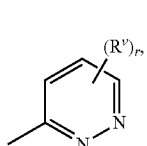

U-41
U-42
U-43
U-44
U-45
U-46
U-47
U-48
U-49
U-50
U-51
U-52

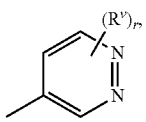
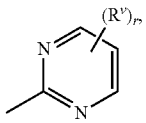
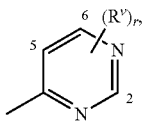
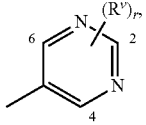
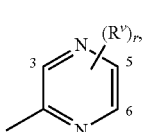
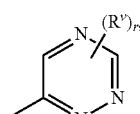
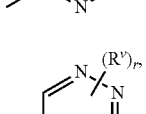
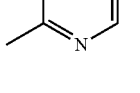
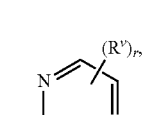
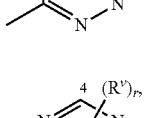

and

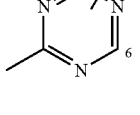

U-53
U-54
U-55
U-56
U-57
U-58
U-59
U-60
U-61

As noted above, $Q^1$ and $Q^2$ can be (among others) an 8-, 9- or 10-membered heteroaromatic bicyclic ring system optionally substituted with one or more substituents selected from a group of substituents as defined in the Summary of the Invention for $Q^1$ and $Q^2$. Examples of 8-, 9- or 10-membered heteroaromatic bicyclic ring system optionally substituted with from one or more substituents include the rings U-62 through U-100 illustrated in Exhibit 2 wherein $R^v$ is any substituent as defined in the Summary of the Invention for $Q^1$ or $Q^2$, and r is typically an integer from 0 to 4.

Exhibit 2
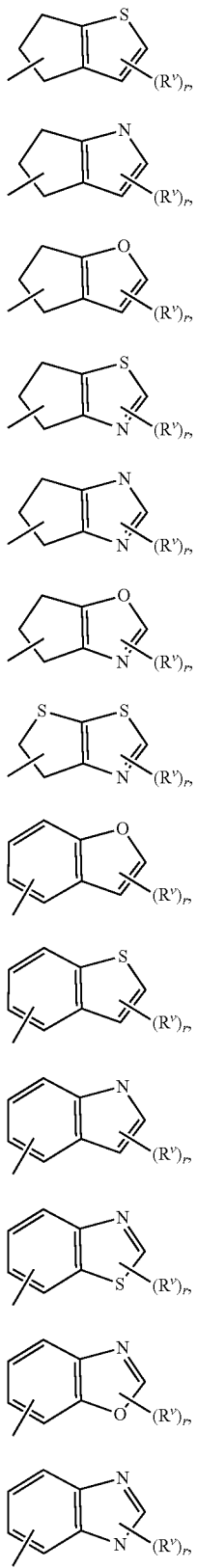
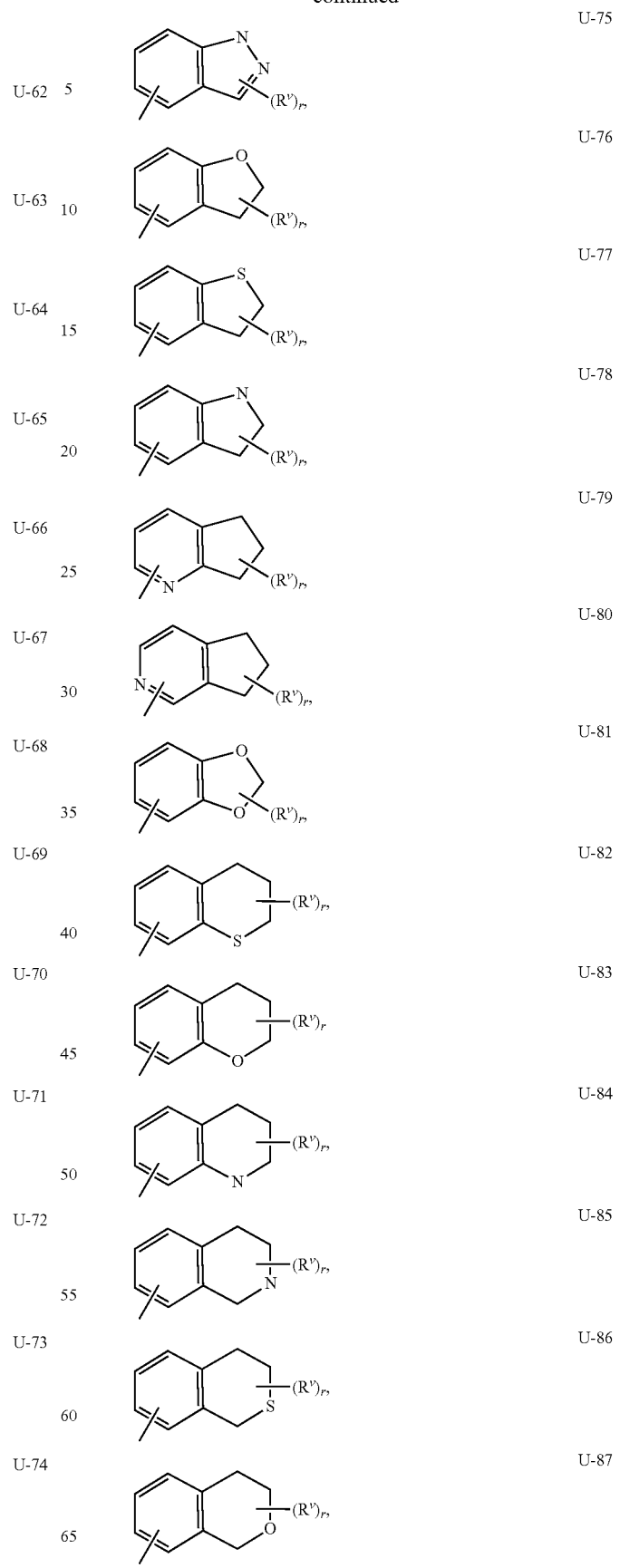

U-88 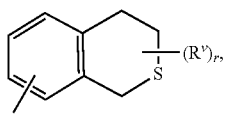

U-89 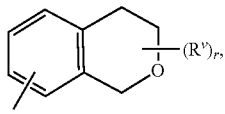

U-90 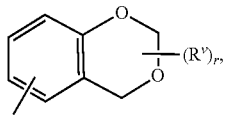

U-91 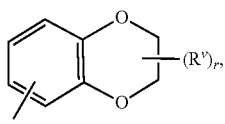

U-92 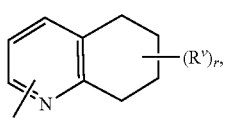

U-93 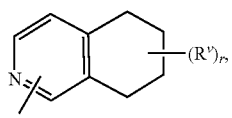

U-94 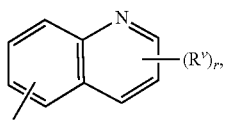

U-95 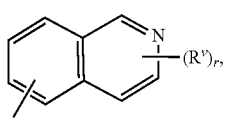

U-96 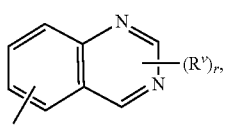

U-97 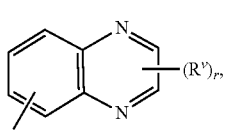

U-98 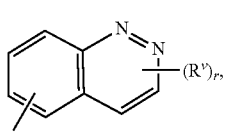

U-99 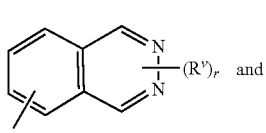 and

U-100 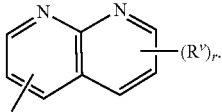

Although $R^v$ groups are shown in the structures U-1 through U-100, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $)(R^v)_r$ and the U group is illustrated as floating, $)(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Preferably for greatest herbicidal activity, the U group is attached to the remainder of Formula 1 through an available carbon or nitrogen on a fully unsaturated ring of the U group. Note that some U groups can only be substituted with less than 5 $R^v$ groups (e.g., U-2 through U-5, U-7 through U-48, and U-52 through U-61).

As noted above, $R^6$ and $Q^2$ can be taken together with the nitrogen atom to which they are both bonded to form an 8- to 10-membered bicyclic ring system. Some examples are shown in Exhibit 3.

Exhibit 3

U-103

U-104 and

U-105

In the present disclosure and claims, the term "piperidinone" and related terms such as "piperidinone ring" refer to 2-oxo-piperidine derivatives according to the Chemical Abstracts system of nomenclature, including derivatives in which the oxygen atom of the 2-oxo moiety is replaced by S or $NR^{12}$ as $Y^1$, unless limited to oxygen by particular context.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Compre-* hensive *Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. Particularly when $R^4$ and $R^5$ are each H, the $C(=Y^2)N(Q^2)(R^6))$ and $Q^1$ substituents are typically mostly in the thermodynamically preferred trans configuration on the piperidinone ring.

For example, as shown in the following, the $C(O)N(Q^2)(R^6)$ moiety (i.e. in Formula 1 wherein both $Y^1$ and $Y^2$ are O; and J is $-CR^2R^3-$ and $R^2$ and $R^3$ are both H) bonded to the carbon at the 3-position of the cyclic amide ring and $Q^1$ bonded to the carbon at the 4-position of the piperidinone ring are generally found in the trans configuration. These two carbon atoms both possess a chiral center. The most prevalant pair of enantiomers are depicted as Formula 1' and Formula 1". While this invention pertains to all stereoisomers, the preferred enantiomer for biological operability is identified as Formula 1'. For a comprehensive discussion of all aspects of stereoisomerism, see Ernest L. Eliel and Samuel H. Wilen, *Stereochemistry of Organic Compounds*, John Wiley & Sons, 1994.

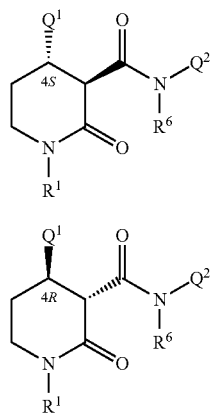

The skilled artisan will also recognize that the carbon atom at the 5- or 6-position of the piperidinone ring also contains a stereocenter indicated by a (*) as shown in Formula 1'". This invention pertains to all stereoisomers, and therefore, when either $R^2$ and $R^3$, or $R^{2A}$ and $R^{3A}$ are other than the same substituent, then a mixture of diastereomers is possible.

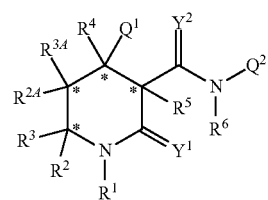

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention also comprises racemic mixtures, for example, equal amounts of the enantiomers of Formulae 1' and 1" (and optionally 1'"). In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enentiomeric ratio (ER) expressed as the relative area % of the two entantiomers determined by chiral high-performance liquid chromatography.

Preferably the compositions of this invention have at least a 50% ER; more preferably at least a 75% ER; still more preferably at least a 90% ER; and the most preferably at least a 94% ER of the more active isomer. Of particular note are enantiomerically pure embodiments of the more active isomer.

Compounds of Formula 1 can comprise additional chiral centers. For example, substituents and other molecular constituents such as $R^2$, $R^3$ and $R^6$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond $C(O)N(Q^2)(R^6)$ in Formula 1. This invention comprises mixtures of conformational isomers. In addition, this invention includes compounds that are enriched in one conformer relative to others. Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium.

Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1. A compound of Formula 1 wherein $Q^1$ is a phenyl ring optionally substituted with up to 5 substituents independently selected from $R^7$.

Embodiment 2. A compound of Embodiment 1 wherein $Q^1$ is a phenyl ring substituted with 1 to 3 substituents independently selected from $R^7$.

Embodiment 3. A compound of Embodiment 2 wherein $Q^1$ is a phenyl ring substituted with 1 to 2 substituents independently selected from $R^7$.

Embodiment 4. A compound of Formula 1 or any one of Embodiments 1 through 3 wherein $Q^1$ is a phenyl ring having a substituent selected from $R^7$ at a meta (e.g., 3-) position or the para (4-) position (and optionally other substituents).

Embodiment 5. A compound of Embodiment 4 wherein $Q^1$ is a phenyl ring having a substituent selected from $R^7$ at a meta position (and optionally other substituents).

Embodiment 6. A compound of Embodiment 4 wherein $Q^1$ is a phenyl ring having a substituent selected from $R^7$ at the para position (and optionally other substituents).

Embodiment 7. A compound of Formula 1 or any one of Embodiments 1 through 6 wherein when $Q^1$ is a phenyl ring substituted with at least two substituents selected from $R^7$, then one substituent is at a meta position and at least one other substituent is at the adjacent para position (of the phenyl ring).

Embodiment 8. A compound of Formula 1 or any one of Embodiments 1 through 7 wherein $Q^1$ is a phenyl ring substituted with 1 substituent selected from $R^7$ at a meta position or the para position or substituted with 2 substituents independently selected from $R^7$ wherein one substituent is at a meta position and the other substituent is at the adjacent para position.

Embodiment 9. A compound Embodiment 8 wherein $Q^1$ is a phenyl ring substituted with 1 substituent selected from $R^7$ at a meta position or substituted with 2 substituents independently selected from $R^7$ wherein one substituent is at a meta position and the other substituent is at the adjacent para position.

Embodiment 10. A compound of Embodiment 8 wherein $Q^1$ is a phenyl ring substituted with 1 substituent selected from $R^7$ at the para position or substituted with 2 substituents independently selected from $R^7$ wherein one substituent is at a meta position and the other substituent is at the adjacent para position.

Embodiment 11. A compound of Formula 1 or any one of Embodiments 1 through 10 wherein $Q^2$ is a phenyl ring substituted with up to 5 substituents independently selected from $R^{10}$.

Embodiment 12. A compound of Embodiment 11 wherein $Q^2$ is a phenyl ring substituted with 1 to 3 substituents independently selected from $R^{10}$.

Embodiment 13. A compound of Embodiment 12 wherein $Q^2$ is a phenyl ring substituted with 1 to 2 substituents independently selected from $R^{10}$.

Embodiment 14. A compound of Formula 1 or any one of Embodiments 1 through 13 wherein $Q^2$ is a phenyl ring having at least one substituent selected from $R^{10}$ at an ortho (e.g., 2-) position (and optionally other substituents).

Embodiment 15. A compound of Formula 1 or any one of Embodiments 1 through 14 wherein when $Q^2$ is a phenyl ring substituted with at least two substituents selected from $R^{10}$, then at least one substituent is at an ortho position and at least one substituent is at the adjacent meta position (of the phenyl ring).

Embodiment 16. A compound of Formula 1 or any one of Embodiments 1 through 15 wherein $Q^2$ is a phenyl ring substituted with 1 substituent selected from $R^{10}$ at an ortho position or substituted with 2 substituents independently selected from $R^{10}$ wherein one substituent is at an ortho position and the other substituent is at the adjacent meta position.

Embodiment 17. A compound of Formula 1 or any one of Embodiments 1 through 16 wherein each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, $C_1$-$C_4$ alkylamino, $C_2$-$C_4$ dialkylamino, formylamino, $C_2$-$C_4$ alkylcarbonylamino, —SF$_5$, —SCN, $C_3$-$C_4$ trialkylsilyl, trimethylsilylmethyl or trimethylsilylmethoxy.

Embodiment 18. A compound of Embodiment 17 wherein each $R^7$ is independently halogen, cyano, $C_1$-$C_2$ alkyl, $C_1$-$C_3$ haloalkyl or $C_1$-$C_3$ alkylsulfonyl.

Embodiment 19. A compound of Embodiment 18 wherein each $R^7$ is independently halogen or $C_1$-$C_2$ haloalkyl.

Embodiment 20. A compound of Embodiment 19 wherein each $R^7$ is independently halogen or $C_1$ haloalkyl.

Embodiment 21. A compound of Embodiment 20 wherein each $R^7$ is independently halogen or $C_1$ fluoroalkyl.

Embodiment 22. A compound of Embodiment 21 wherein each $R^7$ is independently halogen or CF$_3$.

Embodiment 23. A compound of Embodiment 22 wherein each $R^7$ is independently F, Cl, Br or CF$_3$.

Embodiment 24. A compound of Embodiment 23 wherein each $R^7$ is independently F or CF$_3$.

Embodiment 25. A compound of Embodiment 23 or 24 wherein at most only one CF$_3$ substituent is present and is at a meta position or the para position of the $Q^1$ phenyl ring.

Embodiment 26. A compound of Embodiment 25 wherein at most only one CF$_3$ substituent is present and is at a meta position of the $Q^1$ phenyl ring.

Embodiment 27. A compound of Embodiment 25 wherein at most only one CF$_3$ substituent is present and is at the para position of the $Q^1$ phenyl ring.

Embodiment 28. A compound of any one of Embodiments 17 through 27 wherein each $R^{10}$ is independently halogen, cyano, nitro, $C_1$-$C_2$ alkyl, $C_1$-$C_3$ haloalkyl or $C_1$-$C_3$ alkylsulfonyl.

Embodiment 29. A compound of Embodiment 28 wherein each $R^{10}$ is independently halogen or $C_1$-$C_2$ haloalkyl.

Embodiment 30. A compound of Embodiment 29 wherein each $R^{10}$ is independently halogen or $C_1$ haloalkyl.

Embodiment 31. A compound of Embodiment 30 wherein each $R^{10}$ is independently halogen or $C_1$ fluoroalkyl.

Embodiment 32. A compound of Embodiment 31 wherein each $R^{10}$ is independently halogen or CF$_3$.

Embodiment 33. A compound of Embodiment 32 wherein each $R^{10}$ is independently F, Cl, Br or CF$_3$.

Embodiment 34. A compound of Embodiment 33 wherein each $R^{10}$ is independently F or CF$_3$.

Embodiment 35. A compound of Embodiment 34 wherein each $R^{10}$ is F.

Embodiment 36. A compound of Formula 1 or any one of Embodiments 1 through 35 wherein, independently, each $R^9$ and $R^{11}$ is independently H or $C_1$-$C_2$ alkyl.

Embodiment 37. A compound of Embodiment 36 wherein, independently, each $R^9$ and $R^{11}$ is CH$_3$.

Embodiment 38. A compound of Formula 1 or any one of Embodiments 1 through 37 wherein $Y^1$ is O.

Embodiment 39. A compound of Formula 1 or any one of Embodiments 1 through 38 wherein $Y^2$ is O.

Embodiment 39a. A compound of Formula 1 or any one of Embodiments 1 through 38 wherein $R^1$ is H or $C_1$-$C_6$ alkyl.

Embodiment 40. A compound of Embodiment 39a wherein $R^1$ is H or CH$_3$.

Embodiment 41. A compound of Embodiment 40 wherein $R^1$ is H.

Embodiment 41a. A compound of Embodiment 40 wherein $R^1$ is CH$_3$.

Embodiment 42. A compound of Formula 1 or any one of Embodiments 1 through 41a wherein $R^2$ is H or CH$_3$.

Embodiment 43. A compound of Embodiment 42 wherein $R^2$ is H.

Embodiment 44. A compound of Formula 1 or any one of Embodiments 1 through 43 wherein $R^3$ is H or CH$_3$.

Embodiment 45. A compound of Embodiment 44 wherein $R^3$ is H.

Embodiment 46. A compound of Formula 1 or any one of Embodiments 1 through 45 wherein $R^{2A}$ is H or CH$_3$.

Embodiment 47. A compound of Embodiment 46 wherein $R^{2A}$ is H.

Embodiment 48. A compound of Formula 1 or any one of Embodiments 1 through 47 wherein $R^{3A}$ is H or CH$_3$.

Embodiment 49. A compound of Embodiment 48 wherein $R^{3A}$ is H.

Embodiment 50. A compound of Formula 1 or any one of Embodiments 1 through 49 wherein $R^4$ is H or CH$_3$.

Embodiment 51. A compound of Embodiment 50 wherein $R^4$ is H.

Embodiment 52. A compound of Formula 1 or any one of Embodiments 1 through 51 wherein $R^5$ is H or CH$_3$.

Embodiment 53. A compound of Embodiment 52 wherein $R^5$ is H.

Embodiment 54. A compound of Formula 1 or any one of Embodiments 1 through 53 wherein $R^6$ is H or CH$_3$.

Embodiments of this invention, including Embodiments 1-54 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-54 above as well as any other embodiments described herein, and any combination thereof, pertain to the compositions and methods of the present invention.

Combinations of Embodiments 1-54 are illustrated by:

Embodiment A. A compound of Formula 1 wherein
each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy; and
each $R^9$ and $R^{11}$ is independently H or $C_1$-$C_2$ alkyl.

Embodiment B. A compound of Embodiment A wherein
$Y^1$ and $Y^2$ are each O;
$R^1$ is H or $C_1$-$C_6$ alkyl; and
$R^2$, $R^3$, $R^{2A}$, $R^{3A}$, $R^4$, $R^5$ and $R^6$ are each H.

Embodiment C. A compound of Embodiment B wherein $R^1$ is H or Me.

Embodiment D. A compound of Embodiment C wherein
$Q^1$ is a phenyl ring substituted with 1 to 3 substituents independently selected from $R^7$; and
$Q^2$ is a phenyl ring substituted with 1 to 3 substituents independently selected from $R^{10}$.

Embodiment E. A compound of Embodiment D wherein
each $R^7$ is independently halogen, cyano, $C_1$-$C_2$ alkyl, $C_1$-$C_3$ haloalkyl or $C_1$-$C_3$ alkylsulfonyl; and
each $R^{10}$ is independently halogen, cyano, nitro, $C_1$-$C_2$ alkyl, $C_1$-$C_3$ haloalkyl or $C_1$-$C_3$ alkylsulfonyl.

Embodiment F. A compound of Embodiment E wherein
$Q^1$ is a phenyl ring substituted with 1 substituent selected from $R^7$ at a meta position or the para position or substituted with 2 substituents independently selected from $R^7$ wherein one substituent is at a meta position and the other substituent is at the para position; and
$Q^2$ is a phenyl ring substituted with 1 substituent selected from $R^{10}$ at an ortho position or substituted with 2 substituents independently selected from $R^{10}$ wherein one substituent is at an ortho position and the other substituent is at the adjacent meta position.

Embodiment G. A compound of Embodiment F wherein
each $R^7$ is independently F or $CF_3$; and
each $R^{10}$ is F.

Specific embodiments include compounds of Formula 1 selected from the group consisting of:

N-(2,3-difluorophenyl)-2-oxo-4-[3-(trifluoromethyl)phenyl]-3-piperidinecarboxamide (Compound 9);

2-oxo-N-[2-(trifluoromethyl)phenyl)-4-[3-(trifluoromethyl)phenyl]-3-piperidinecarboxamide (Compound 10);

N-(2,3-difluorophenyl)-2-oxo-4-[4-(trifluoromethyl)phenyl]-3-piperidinecarboxamide (Compound 11);

(3S,4S)—N-(2,3-difluorophenyl)-4-(4-fluorophenyl)-1-methyl-2-oxo-3-piperidinecarboxamide (Compound 52);

4-[3-(difluoromethyl)phenyl]-N-(2,3-difluorophenyl)-2-oxo-3-piperidinecarboxamide (Compound 49);

(3R,4S)-4-(3-chlorophenyl)-N-(2,3-difluorophenyl)-2-oxo-3-piperidinecarboxamide (Compound 42);

4-(3-chlorophenyl)-N-(2,3-difluorophenyl)-2-oxo-3-piperidinecarboxamide (Compound 36);

2-oxo-4-[3-(trifluoromethyl)phenyl]-N-(2,3,4-trifluorophenyl)-3-piperidinecarboxamide (Compound 30);

(3R,4S)—N-(3-chloro-2-fluorophenyl)-2-oxo-4-[3-(trifluoromethyl)phenyl]-3-piperidinecarboxamide (Compound 25);

(3R,4S)—N-(2,3-difluorophenyl)-2-oxo-4-[4-(trifluoromethyl)phenyl]-3-piperidinecarboxamide (Compound 22); and (3R,4S)—N-(2,3-difluorophenyl)-2-oxo-4-[3-(trifluoromethyl)phenyl]-3-piperidinecarboxamide (Compound 21).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltranspererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine. Of note is a compound of the invention mixed with atrazine, bromoxynil or metribuzin.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron. Of note is a compound of the invention mixed with nicosulfuron, flupyrsulfuron or chlorimuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl. Of note is a compound of the invention mixed with pinoxaden or quizalofop.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate. Of note is a compound of the invention mixed with dicamba.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4, 5-dihydro-5,5-dimethylisoxazole), fentrazamide, flufenacet, indanofan, mefenacet, metazachlor, metolachlor, napronilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides. Of note is a compound of the invention mixed with flufenacet.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b1) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3 (2H)-pyridazinone, 4-(4-fluorophenyl)-6-[(2-hydroxy-6-oxo-1-cyclohexen-1-yl)carbonyl]-2-methyl-1,2,4-triazine-3,5(2H, 4H)-dione, 5-[(2-hydroxy-6-oxo-1-cyclohexen-1-yl)carbonyl]-2-(3-methoxyphenyl)-3-(3-methoxypropyl)-4 (3H)-pyrimidinone, 2-methyl-N-(4-methyl-1,2,5-oxadiazol-3-yl)-3-(methylsulfinyl)-4-(trifluoromethyl)benzamide and 2-methyl-3-(methyl sulfonyl)-N-(1-methyl-1H-tetrazol-5-yl)-4-(trifluoromethyl)benzamide. Of note is a compound of the invention mixed with mesotrione or pyrasulfatole.

HST (homogentisate solenesyltransererase) inhibitors (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3, 5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3 (2H)-pyridazinone.

HST inhibitors also include compounds of Formulae A and B.

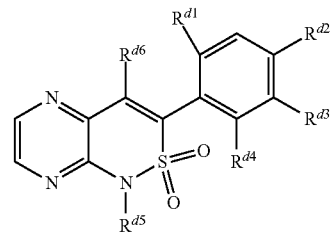

A

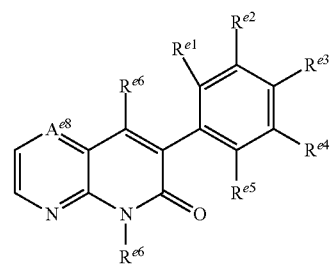

B wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(═O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(═O)Et, —OC(═O)-i-Pr or —OC(═O)-t-Bu; and $A^{e8}$ is N or CH.

Cellulose biosynthesis inhibitors (b14) inhibit the biosynthesis of cellulose in certain plants. They are most effective when using a pre-application or early post-application on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

Other herbicides (b15) include herbicides that act through a variety of different modes of action such as mitotic disruptors (e.g., flamprop-M-methyl and flamprop-M-isopropyl) organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro-[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide. Of note is 2-methoxy-N-[[4-[[(methylamino)carbonyl]amino]phenyl]sulfonyl]-benzamide (alternatively named N-(2-methoxybenzoyl)-4-[(methylaminocarbonyl)amino]benzenesulfonamide; CAS #129531-12-0) mixed with any one of the compounds listed in Index Tables A.

The compounds of Formula 1 can be prepared by general methods known in the art of synthetic organic chemistry. Of note are the following methods described in Schemes 1-15 and variations thereof. The definitions of $R^1$, $R^2$, $R^3$, $R^{2A}$, $R^{3A}$, $R^4$, $R^5$, $R^6$, $Q^1$, $Q^2$, $Y^1$, and $Y^2$ in the compounds of Formulae 1 through 19 below are as defined above in the Summary of the Invention unless otherwise noted. Formulae 1a-1h and 5a and 10a are various subsets of a compound of Formulae 1, 5 and 10 respectively. Substituents for each subset formula are as defined for its parent formula unless otherwise noted.

As shown in Scheme 1 a compound of Formula 1a (i.e. Formula 1 wherein $R^1$, $R^2$, $R^3$, $R^4$ and $R^5$ are H, and $Y^1$ and $Y^2$ are O) can be prepared by reaction of acids of Formula 2 with amines of Formula 3 in the presence of a dehydrative coupling reagent such as propylphosphonic anhydride, dicyclohexylcarbodiimide, N-(3-dimethylaminopropyl)-N-ethylcarbodiimide, N,N-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0-60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride. The method of Scheme 1 utilizing propylphosphonic anhydride is illustrated by Step E of Synthesis Example 1. Substituents in the 3- and 4-positions of the piperidinone ring of compounds of Formula 1a, i.e. C(=O)N($Q^2$)($R^6$) and $Q^1$, respectively, are predominantly in the trans configuration.

Scheme 1

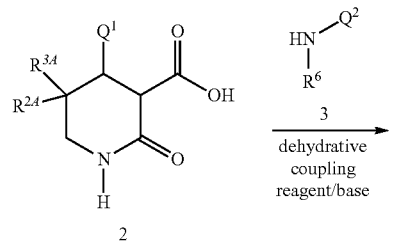

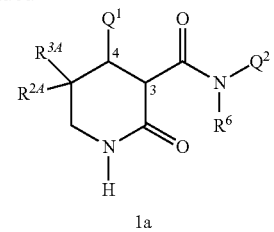

1a

As shown in Scheme 2 a compound of Formula 2 can be prepared by hydrolysis of esters of Formula 4 by methods well known to those skilled in the art. Hydrolysis is carried out with aqueous base or aqueous acid, typically in the presence of a co-solvent. Suitable bases for the reaction include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. and the boiling point of the solvent, and typically from 0 to 100° C. The method of Scheme 2 is illustrated by Step D of Synthesis Example 1.

Scheme 2

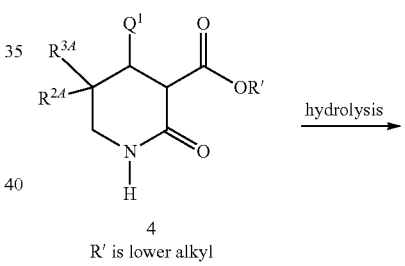

R' is lower alkyl

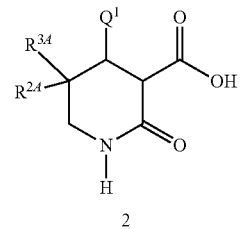

2

As shown in Scheme 3, a compound of Formula 4 can be obtained by reduction of a compound of Formula 5 and subsequent in situ cyclization of the resulting intermediate amine. A wide variety of methods for reduction of the aliphatic nitrile group in a compound of Formula 5 are known in the literature. Methods well known to those skilled in the art include catalytic hydrogenation in the presence of Raney nickel and lithium aluminum hydride. The method of Scheme 3 is illustrated by Step C of Synthesis Example 1.

Scheme 3

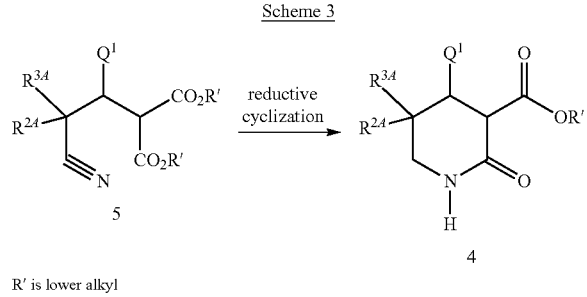

R' is lower alkyl

As shown in Scheme 4, a compound of Formula 5 can be prepared by reacting diesters of Formula 6 with nitriles of Formula 7, typically in the presence of a base. Suitable bases for the reaction include alkali metal lower alkoxides such as sodium methoxide in methanol or sodium ethoxide in ethanol. Bases such as lithium hexamethyldisilazide in tetrahydrofuran are also useful. The method of Scheme 4 is illustrated by Step B of Synthesis Example 1. A compound of Formula 6 can readily be prepared by methods known to those skilled in the art, e.g., by Knoevenagel condensation of aldehydes and malonates (see for example G. Jones, *Organic Reactions Volume* 15, John Wiley and Sons, 1967).

Scheme 4

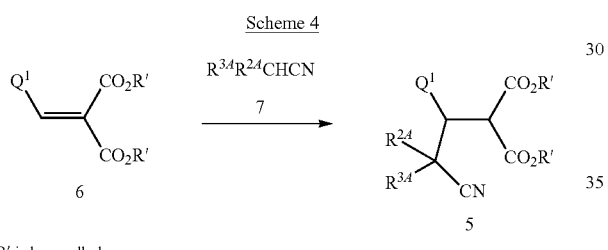

R' is lower alkyl

A compound of Formula 5a (i.e. Formula 5 wherein $R^{2A}$ and $R^{3A}$ are H) can be prepared by reacting a compound of Formula 8 with malonates of Formula 9 in the presence of a base as shown in Scheme 5. Suitable bases for this reaction include, but are not limited to, alkali metal lower alkoxides such as sodium methoxide in methanol or sodium ethoxide in ethanol, or bases such as lithium bis(trimethylsilyl)amide, sodium bis(trimethylsilyl)amide and lithium diisopropylamide in solvents such as tetrahydrofuran. Typically, the reaction is carried out in the range of from −78° C. to 23° C. Cyanoalkenes of Formula 8 can readily be prepared from aldehydes and acetonitrile by methods known to those skilled in the art.

Scheme 5

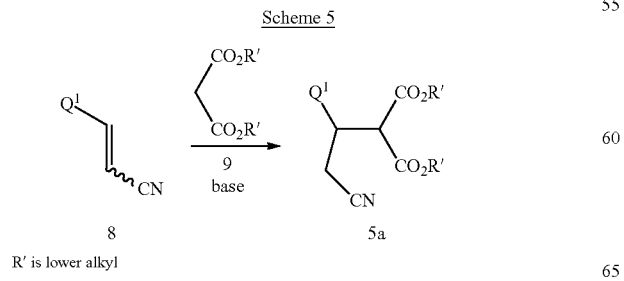

R' is lower alkyl

As shown in Scheme 6 a compound of Formula 1a can also be prepared by reductive cyclization of a compound of Formula 10 analogous to the method of Scheme 3. As also shown in Scheme 6, a compound of Formula 1b (i.e. Formula 1 wherein $R^1$ is OH, $R^{2A}$, $R^{3A}$ $R^4$ and $R^5$ are H, and $Y^1$ and $Y^2$ are O) can be prepared from a compound of Formula 10 by catalytic transfer hydrogenation with ammonium formate in the presence of palladium on carbon, and subsequent in situ cyclization of the intermediate hydroxylamine. See *J. Med. Chem.* 1993, 36, 1041-1047 for catalytic transfer hydrogenation/cyclization conditions to produce N-hydroxypiperidinones.

Scheme 6

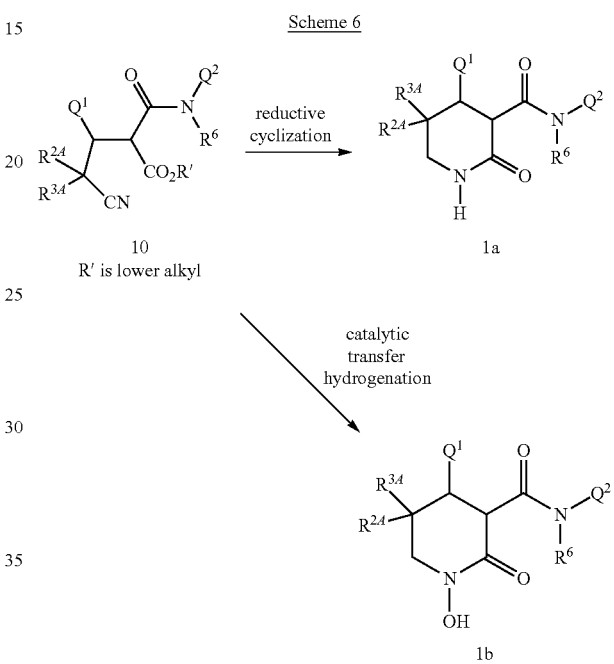

R' is lower alkyl

As shown in Scheme 7, a compound of Formula 10 can be prepared by reacting a compound of Formula 11 with nitriles of Formula 7 in a solvent, in the presence of a base analogous to the method described in Scheme 4.

Scheme 7

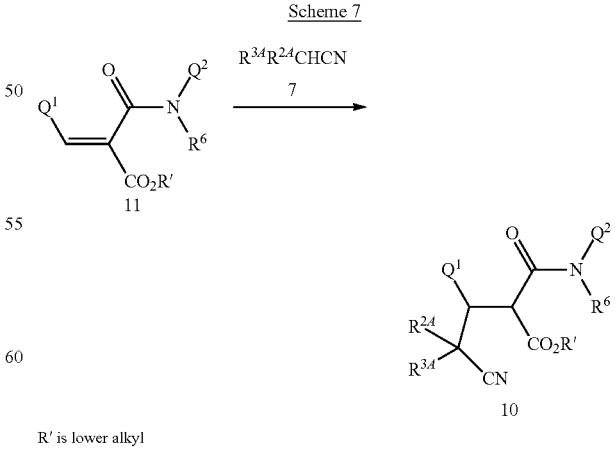

R' is lower alkyl

As shown in Scheme 8, a compound of Formula 10a (i.e. Formula 10 wherein $R^{2A}$ and $R^{3A}$ are H) can be prepared, analogous to the method of Scheme 5, by reacting cyano-alkenes of Formula 8 with malonates of Formula 12.

Scheme 8

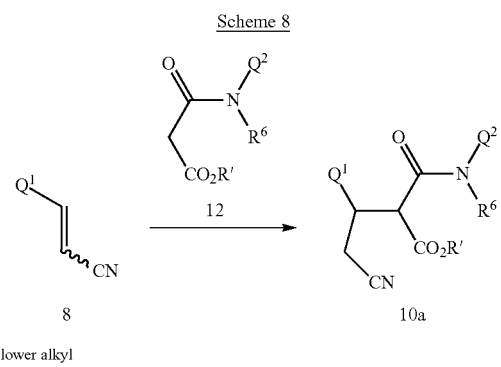

R' is lower alkyl

As shown in Scheme 9, a compound of Formula 11 can be prepared by reaction of malonates of Formula 12 with aldehydes of Formula 14 by methods known to those skilled in the art. As also shown in Scheme 9, malonates of Formula 12 can readily be prepared from lower alkyl malonyl chlorides of Formula 13 such as methyl malonyl chloride and amines of Formula 3 by methods known to those skilled in the art.

Scheme 9

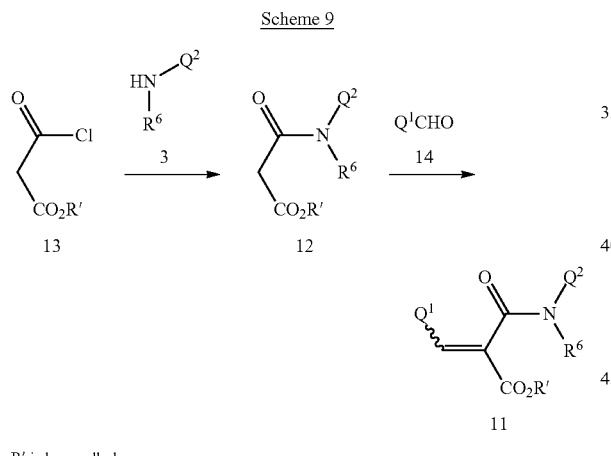

R' is lower alkyl

As shown in Scheme 10, mixtures of a compound of Formula 1c (i.e. Formula 1 wherein $R^1$, $R^2$, $R^3$ and $R^5$ are H, $R^4$ is halogen and $Y^1$ and $Y^2$ are O) and Formula 1d (i.e. Formula 1 wherein $R^1$, $R^2$, $R^3$ and $R^4$ are H, $R^5$ is halogen and $Y^1$ and $Y^2$ are O) can be prepared by reacting a compound of Formula 1a with a halogen source in a solvent, in the presence or absence of an initiator. Separation of the regioisomers produced in this reaction can be achieved by standard methods such as chromatography or fractional crystallization. Suitable halogen sources for this reaction include bromine, chlorine, N-chlorosuccinimide, N-bromosuccinimide and N-iodosuccinimide. Suitable initiators for this reaction include 2,2'-azobisisobutyronitrile (AIBN) and benzoyl peroxide. Typically, the reaction is carried out in solvents such as dichloromethane in the range of from 0° C. to the boiling point of the solvent.

Scheme 10

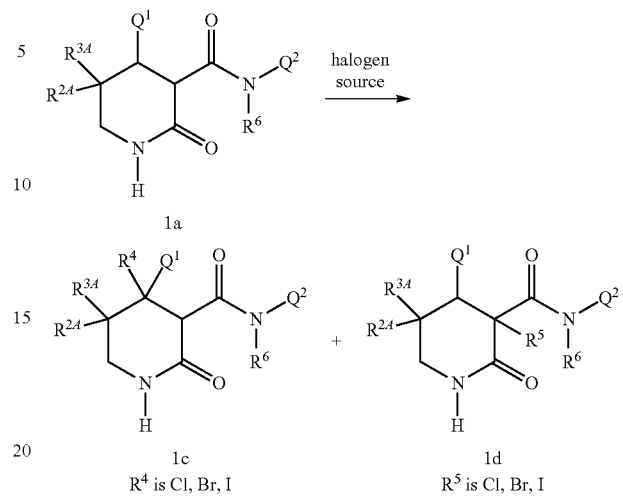

$R^4$ is Cl, Br, I    $R^5$ is Cl, Br, I

As shown in Scheme 11, a compound of Formula 1e (i.e. Formula 1 wherein $R^1$ is $NH_2$, $R^2$, $R^3$, $R^4$ and $R^5$ are H and $Y^1$ and $Y^2$ are O) can be prepared by reacting a compound of Formula 1a with an aminating reagent such as O-(diphenylphosphinyl)hydroxylamine and hydroxylamino-O-sulphonic acid. For procedures, conditions and reagents see *Bioorganic & Medicinal Chemistry Letters* 2009, 19, 5924-5926 and *J. Org. Chem.* 2002, 67, 6236-6239.

Scheme 11

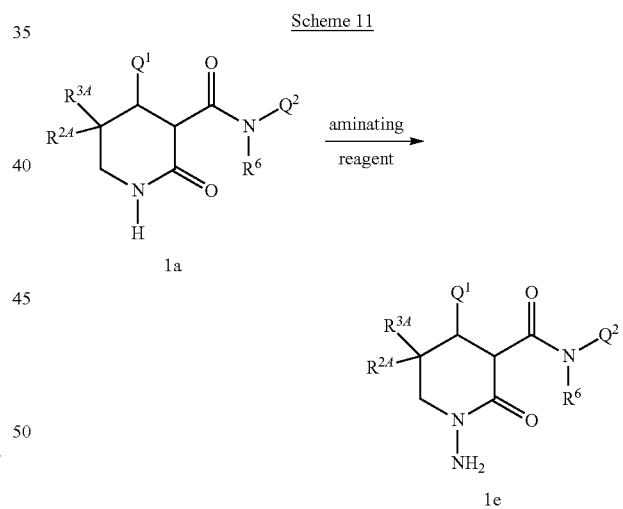

As shown in Scheme 12, a compound of Formula 1f (i.e. Formula 1 wherein $R^2$, $R^3$, $R^4$, $R^5$ and $R^6$ are H and $Y^1$ is O) can be produced by reaction of compounds of Formula 15 with isocyanates (i.e. a compound of Formula 16 wherein $Y^2$ is O) or isothiocyanates (i.e. a compound of Formula 16 wherein $Y^2$ is S) in the presence of base. Examples of the base which can be used for the present process include those listed for the method of Scheme 4. The reaction temperature can be selected from the range of from −78° C. to the boiling point of an inert solvent used. Typically, the reaction is carried out at temperatures ranging from −78° C. to 100° C. in solvents such as toluene.

Scheme 12

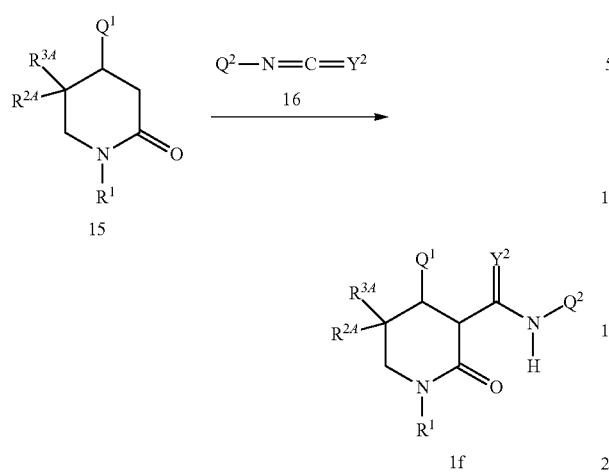

As shown in Scheme 13, compounds of Formula 15 can be prepared by reaction of a compound of Formula 17 with corresponding electrophiles of Formula 18 in the presence of base. In Formula 18, G denotes a leaving group, i.e. a nucleofuge. Depending upon selection of $R^1$, suitable electrophiles for the reaction can include alkyl halides such as chlorides, bromides and iodides, alkylsulfonates, acid anhydrides such as tert-butoxycarbonyl anhydride and acetic anhydride, and haloalkylsilanes such as chlorotrimethylsilane. Suitable bases for the reaction include inorganic bases such as alkali or alkaline earth metal (e.g., lithium, sodium, potassium and cesium) hydroxides, alkoxides, carbonates, and phosphates, and organic bases such as triethylamine, N,N-diisopropylethylamine and 1,8-diazabicyclo[5.4.0]undec-7-ene. A wide variety of solvents are suitable for the reaction including, for example but not limited to, tetrahydrofuran, dichloromethane, N,N-dimethylformamide, N,N-dimethylacetamide, N-methylpyrrolidinone, acetonitrile, $C_2$-$C_6$ alcohols and acetone as well as mixtures of these solvents. This reaction is conducted at temperatures ranging from −20 to 200° C., and typically between 0 and 50° C.

Scheme 13

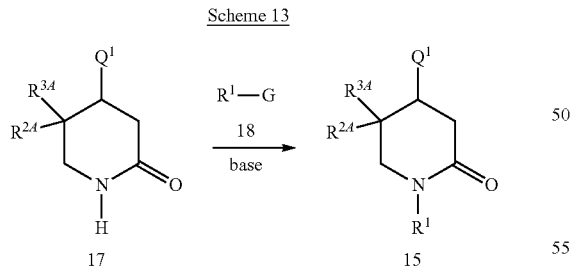

As shown in Scheme 14, a compound of Formula 1g (i.e. a compound of Formula 1 wherein $R^1$, $R^2$, $R^3$, $R^4$ and $R^5$ are H, and $Y^1$ and $Y^2$ are S) can be prepared by reacting a compound of Formula 1a with at least two equivalents of a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C. One skilled in the art recognizes that using less than two equivalents of the thionating reagent can provide mixtures comprising s compound of Formula 1 products wherein $Y^1$ is O and $Y^2$ is S, or $Y^1$ is S and $Y^2$ is O, which can be separated by conventional methods such as chromatography and crystallization.

Scheme 14

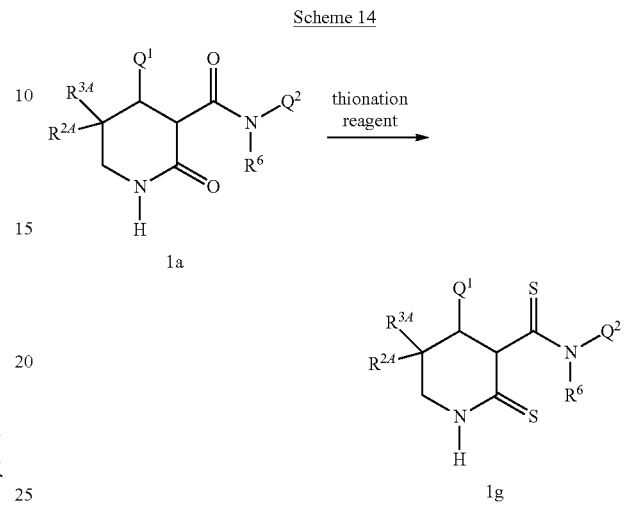

As shown in Scheme 15, a compound of Formula 1h (i.e. a compound of Formula 1 wherein $R^1$, $R^2$, $R^3$, $R^4$, and $R^5$ are H, $Y^2$ is O and $Y^1$ is NH) can be prepared by alkylation of a compound of Formula 1a triethyloxonium tetrafluoroborate (Meerwein's reagent) followed by treatment of the resulting imino ether of Formula 19 with aqueous ammonia.

Scheme 15

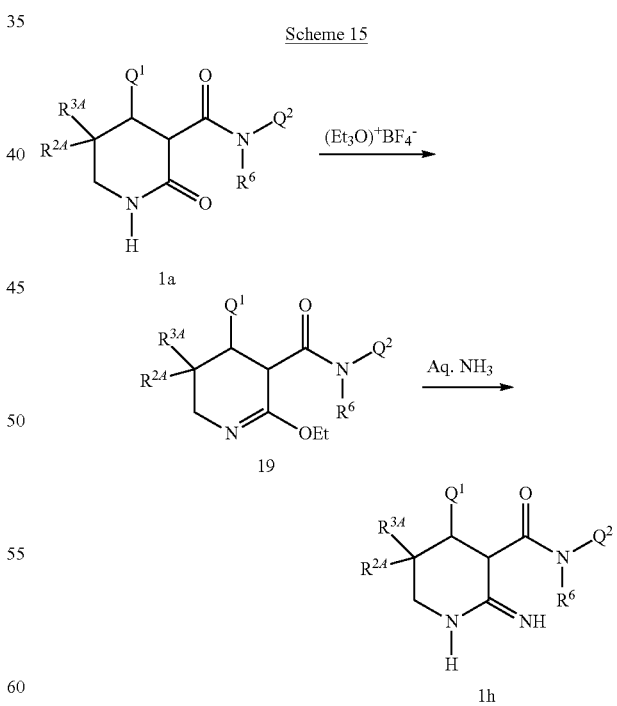

As shown in Scheme 16, a compound of Formula 1a can be alternatively prepared from a compound of Formula 1i (i.e. a subset of Formula 1, wherein $R^1$ is a protecting group, PG). Suitable protecting groups for this transformation include substituted or unsubstituted alkoxy, benzyloxy or benzyl groups. Of note as a protecting group is PMB group (i.e. p-methoxybenzyl group). Removal of the protecting group from a compound of Formula 1i may be accomplished by various means. For example, removal of a methoxy protecting group may be accomplished using $Mo(CO)_6$ or $SmI_2$ as described by Wardrup in *Synlett* 2003, 9, 1352 and *Tetrahedron Lett.* 2004, 45(22), 4229, respectively. Methoxy protecting groups can also be removed via catalytic hydrogenation as described by Takahashi, *Chem. Eur. J.* 2006, 12(22), 5868. Benzyloxy protecting groups are removable by catalytic hydrogenation as described by Panday, *Tetrahedron Lett.* 1995, 36(45), 8205, as well as by $SmI_2$ as described in Langlois, *Tetrahedron Lett.* 2000, 41(43), 8285 or Williams, *Angew. Chem. Int. Ed.* 2005, 44(41), 6715. Benzyl protecting groups may be removed by trifluoroacetic acid (Kudou, EP2336104, p 125), Boron trifluoride etherate (Kawanaka, *Bioorg. Med. Chem.* 2003, 11(8), 1723), $Ce(NH_4)_2(NO_3)_6$ (Yuan, *Bioorg. Med. Chem. Letters,* 2007, 17(6), 1651), DDQ (Fernandez, *J. Org. Chem.* 2004, 69(10), 3562) or catalytic hydrogenation (Tsai, *J. Org. Chem.,* 2005, 70(5), 1780). Other examples of suitable protecting groups and their removal can be found in Wuts, P. G. M.; Greene, T. *Greene's Protective Groups in Organic Synthesis,* 4th ed.; Wiley-Interscience: New Jersey, 2007.

Also as shown in Scheme 16, a compound of Formula 1i can be prepared from a compound of Formula 20 using the same hydrolysis/coupling methods as described in Schemes 1 and 2. One skilled in the art realizes that the hydrolysis, coupling, and deprotection reactions do not necessarily need to follow that specific order, and may be arranged to accommodate particular substrate needs or reactivities.

may then be subsequently reduced and cyclized to provide a compound of Formula 20 after appropriate workup and purification. The amine of Formula 22 generally reacts with a compound of Formula 21 in an alcohol, arene, or ether solvent such as methanol, ethanol, toluene, tetrahydrofuran or dioxane at a temperature ranging from 0° C. to the reflux temperature of the solvent for reaction time ranging from 5 min to 24 h. A dehydrating agent such as $MgSO_4$ or molecular sieves may optionally be used to facilitate formation of an intermediate of Formula 24. The addition of 1-5 equivalents of acid (e.g. $CH_3CO_2H$, $CF_3CO_2H$ or HCl) may facilitate the formation of 24 as well. Although an intermediate of Formula 24 is generally formed in-situ and reduced/cyclized to a compound of Formula 20 in one vessel, isolation of the intermediate of Formula 24 can be done for uptake and reaction in another solvent system for reduction/cyclization to afford a compound of Formula 20 if desired. A variety of protocols use reducing agents for the reduction/cyclization step such as sodium borohydride (Fang, WO2005/044818, p 44), sodium cyanoborohydride (Pichette, *Eur. J. Org. Chem.* 2012, 7, 1328), sodium triacetoxyborohydride ("STAB", Brandau, *Angew. Chem. Int. Ed.,* 2006, 45, 4305), Pyridine/Borane complex (Sakamoto, *J. Org. Chem.* 1994, 59(4), 929), and catalytic hydrogenation (Tietze, *Tetrahedron* 1989, 45, 681).

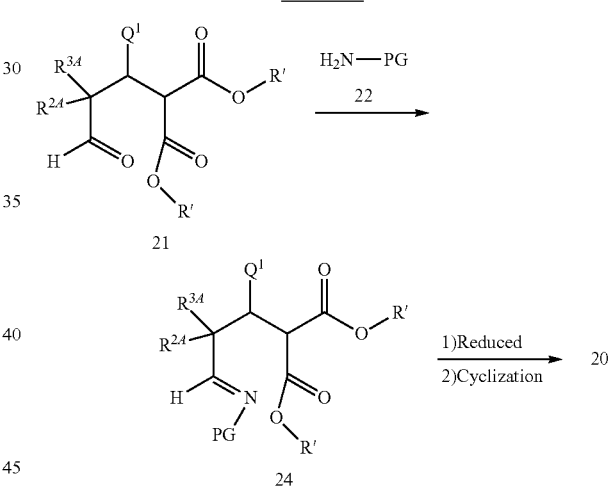

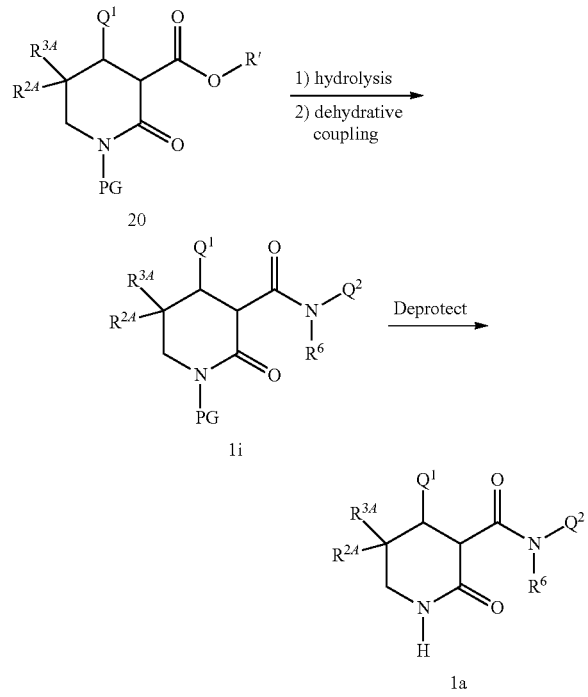

A compound of Formula 20 can be prepared from a compound of Formula 21 as shown in Scheme 17. An amine of the Formula 22 may react with a compound of Formula 21 to generate an intermediate of Formula 24 in-situ, which As shown in Scheme 18, a compound of Formula 4 can alternatively be prepared from a compound of Formula 21 using the method described in WO2005/044818, p 55. A compound of Formula 21 reacts with a compound of Formula 25 in the presence of titanium (IV) ethoxide, followed by treatment with sodium borohydride to afford the sulfonamide intermediate of Formula 26. Subsequent acid deprotection and cyclization of a compound of Formula 26 thereby affords compounds of Formula 4.

Another approach to a compound of Formula 4 is shown in Scheme 18. A compound of Formula 21 may be subjected to biocatalytic reduction using amine transaminases ("ATAs") in accordance with the method described in *Org. Process Res. Dev.* 2014, 18, 215. The reaction may be conducted in a dimethyl sulfoxide/borate buffer solution for 24 to 72 h at a temperature ranging from room temperature to 50° C. using various, commercially-available ATAs (Codexis, Inc, Redwood, Calif., USA). Pyridoxal-5-phosphate is used as the enzyme cofactor, while isopropylamine serves as the amine source.

Alternatively as shown in Scheme 18, a compound of Formula 4 can be prepared from a compound of Formula 21 through a nitrile intermediate of Formula 5. An aldehyde of Formula 21 reacting with hydroxylamine hydrochloride in the presence of sodium iodide at reflux for 0.5 to 24 h using this method is described in Ballini, *Synlett* 2003, 12, 1841. The nitrile intermediate of Formula 5 may then be subjected to reductive cyclization to afford a compound of Formula 4 using the same method as described in Scheme 3.

Formula 21 (see examples in Feu, *Eur. J. Org. Chem.* 2013, 5917 and references therein; and Zhao, *Chem. Commun.* 2013, 49, 7555). In particular, various chiral pyrrolidine bases have been used in this regard for the enantioselective synthesis of a compound of Formula 21' (i.e. a compound of Formula 21 as a specific enantiomer) (see, for examples, Brandau, Angew. *Chem. Int. Ed.,* 2006, 45, 4305; Fang, *Org. Lett.,* 2010, 12(23), 5366; and Ghosh, *Org. Biomol. Chem.* 2012, 10, 8322). The reactions can be run most advanta-

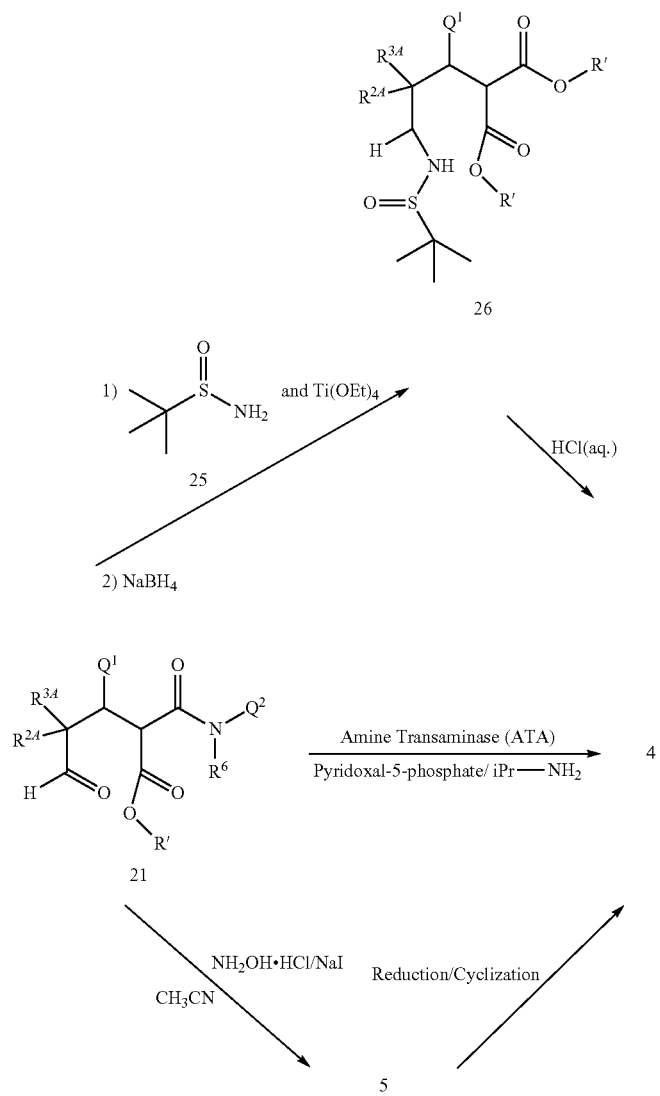

As shown in Scheme 19, a compound of Formula 21' (i.e. a subset of Formula 21, wherein $R^{2A}$ and $R^{3A}$ are both H) can be prepared by reacting of an aldehyde of Formula 23 with malonates of Formula 9 in the presence of a base. The bases such as sodium carbonate and potassium carbonate have been used to accomplish this transformation in arene solvents under phase-transfer conditions (e.g. Kryshtal, *Synthesis,* 1979, 2, 107).

Additionally, recent advances in organocatalysis have shown that various amine bases can also be used for the conversion of a compound of Formula 23 to a compound of Formula 21 (see examples in Feu, *Eur. J. Org. Chem.* 2013, 5917 and references therein; and Zhao, *Chem. Commun.* 2013, 49, 7555). In particular, various chiral pyrrolidine bases have been used in this regard for the enantioselective synthesis of a compound of Formula 21' (i.e. a compound of Formula 21 as a specific enantiomer) (see, for examples, Brandau, *Angew. Chem. Int. Ed.,* 2006, 45, 4305; Fang, *Org. Lett.,* 2010, 12(23), 5366; and Ghosh, *Org. Biomol. Chem.* 2012, 10, 8322). The reactions can be run most advantageously in water or alcoholic solvents at a temperature ranging from 0° C. to ambient temperature for a time ranging from 1 h to 5 d. The amount of pyrrolidine base used ranges from 5%-20 mol % with respect to the malonate of Formula 9. Workup and purification to afford a compound of Formula 21 may be accomplished using the method as described in Brandau, *Angew. Chem. Int. Ed.* 2006, 45, 4305. An aldehyde of Formula 23 is either commercially available or can be prepared using literature methods (see, for example, Battistuzzi, *Org. Lett.* 2003, 5(5), 777). This method is illustrated in Step A of Synthesis Example 4.

Scheme 19

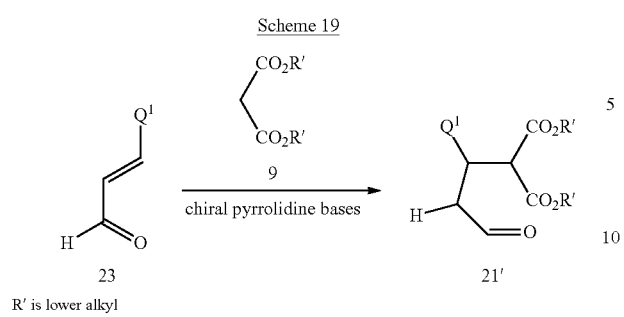

R' is lower alkyl

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of a compound of Formula 1 may contain aromatic nitro groups, which can be reduced to amino groups, and then be converted via reactions well known in the art such as the Sandmeyer reaction, to various halides, providing a compound of Formula 1. The above reactions can also in many cases be performed in alternate order.

It is recognized that some reagents and reaction conditions described above for preparing a compound of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare a compound of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ solution unless indicated otherwise; "s" means singlet, "d" means doublet, "t" means triplet, "q" means quartet, "m" means multiplet and "br s" means broad singlet.

SYNTHESIS EXAMPLE 1

Preparation of N-(2,3-difluorophenyl)-2-oxo-4-[3-(trifluoromethyl)phenyl]-3-piperidinecarboxamide (Compound 9)

Step A: Preparation of 3-[3-(trifluoromethyl)phenyl]-2-propenenitrile

To a stirred mixture of sodium hydride (1.0 g, 43.1 mmol) in tetrahydrofuran (60 mL) at 0° C. was added (cyanomethyl)triphenylphosphonium chloride (11.6 g, 34.4 mmol) in portions and the resulting mixture stirred for 15 min. A solution of 3-(trifluoromethyl) benzaldehyde (5.0 g, 28.7 mmol) in tetrahydrofuran was added dropwise and the resulting reaction mixture stirred for 2 h at room temperature. The reaction mixture was poured into ice cold water and extracted with ethyl acetate. The combined organic extracts were dried (Na$_2$SO$_4$) and concentrated under reduced pressure. The crude product was purified by column chromatography on silica gel eluting with 7% ethyl acetate/petroleum ether to give the title compound (4.0 g).
$^1$H NMR δ 7.8-7.5 (m, 4H), 7.4 (d, 1H), 6.0 (d, 1H).

Step B: Preparation of 1,3-diethyl 2-[2-cyano-1-[3-(trifluoromethyl)phenyl]ethyl]propanedioate To a solution of freshly prepared sodium ethoxide (960 mg), prepared by dissolving sodium metal (41.8 mmol) in ethanol (60 mL), was added diethyl malonate (4.04 g, 25.26 mmol) and the resulting reaction mixture stirred for 10 min at 0° C. A solution of 3-[3-(trifluoromethyl)phenyl]-2-propenenitrile (i.e. the product of Step A, 4.0 g, 21.05 mmol) in ethanol was added dropwise to the reaction mixture at 0° C., the resulting mixture stirred at room temperature for 1 h, and then refluxed for an additional 2 h. The reaction mixture was poured into ice cold water and extracted with ethyl acetate. The combined organic extracts were dried (Na$_2$SO$_4$), and concentrated under reduced pressure. The crude product was purified by column chromatography on silica gel eluting with 10% ethyl acetate/petroleum ether to give the title compound (6.0 g).
$^1$H NMR δ (DMSO-d$_6$) 7.8 (s, 1H), 7.7 (d, 1H), 7.6 (d, 1H), 7.5 (t, 1H), 4.2 (q, 2H), 4.1 (q, 2H), 3.8 (q, 2H), 3.7 (m, 1H), 3.1 (m, 1H), 1.2 (t, 6H).

Step C: Preparation of ethyl 2-oxo-4-[3-(trifluoromethyl)phenyl]-3-piperidinecarboxylate A solution of 1,3-diethyl 2-[2-cyano-1-[3-(trifluoromethyl)phenyl]ethyl]propanedioate (i.e. the product of Step B, 6 g, 16.8 mmol) in ethanol (100 mL) was heated at 100° C. for 16 h in a steel bomb in the presence of Raney nickel (7.47 g, 84.03 mmol) and hydrogen under pressure (40 atm+). The reaction mixture was filtered through a pad of Celite® diatomaceous filter aid and the filtrate was concentrated under reduced pressure. The crude product was triturated with pentane/diethyl ether to give the title compound (3.0 g).
$^1$H NMR (DMSO-d$_6$) δ 7.8 (br s, 1H), 7.7 (d, 1H), 7.6 (d, 2H), 7.5 (t, 1H), 4 (d, 1H), 3.9 (m, 2H), 3.6 (t, 1H), 3.2 (m, 2H), 1.96 (m, 1H), 1.9 (m, 1H), 0.96 (t, 3H).

Step D: Preparation of 2-oxo-4-[3-(trifluoromethyl) phenyl]-3-piperidinecarboxylic acid To a stirred solution of ethyl 2-oxo-4-[3-(trifluoromethyl) phenyl]-3-piperidinecarboxylate (i.e. the product of Step C, 3.0 g, 9.52 mmol) in ethanol (30 mL) at 0° C. was added 50% aqueous sodium hydroxide (2.2 mL, 28.5 mmol) and the resulting mixture stirred at room temperature for 2 h. The reaction mixture was concentrated under reduced pressure, treated with 6 M aqueous hydrochloric acid to adjust the pH to 4-5, and the resulting solid was filtered and washed with diethyl ether to give the title compound as a solid (1.8 g).

$^1$H NMR (DMSO-$d_6$) δ 12.4 (br s, 1H), 7.8 (br s, 1H), 7.6 (d, 2H), 7.4 (d, 2H), 3.6 (d, 1H), 3.4 (m, 1H), 3.2 (m, 1H), 2.01 (m, 1H), 1.9 (m, 1H).

Step E: Preparation of N-(2,3-difluorophenyl)-2-oxo-4-[3-(trifluoromethyl)phenyl]-3-piperidinecarboxamide To a solution of 2-oxo-4-[3-(trifluoromethyl)phenyl]-3-piperidinecarboxylic acid (i.e. the product of Step D, 500 mg, 1.74 mmol) and 2,3-difluoroaniline (270 mg, 2.09 mmol) in N,N-dimethylformamide (20 mL) was added triethylamine (0.75 mL, 5.22 mmol) and propylphosphonic anhydride (830 mg, 2.61 mmol) and the resulting mixture stirred for 16 h at room temperature. The reaction mixture was quenched with water and extracted with ethyl acetate (3×). The combined organic extracts were washed with water, brine, dried ($Na_2SO_4$) and concentrated under reduced pressure. The crude product was purified by chromatography on neutral alumina, eluting with ethyl acetate to give the title compound as solid (300 mg).

$^1$H NMR (DMSO-$d_6$) δ 10.1 (s, 1H), 7.9 (br s, 1H), 7.7-7.4 (m, 5H), 7.2-7.0 (m, 2H), 3.8 (d, 1H), 3.6 (t, 1H), 3.4-3.2 (m, 2H), 2.01-1.98 (m, 2H).

SYNTHESIS EXAMPLE 2

Preparation of N-(2-fluorophenyl)-2-oxo-4-[4-(trifluoromethyl)phenyl]-3-piperidinecarboxamide (Compound 14)

Using the method of Example 1, 2-oxo-4-[4-(trifluoromethyl)phenyl]-3-piperidinecarboxylic acid and 2-fluoroaniline afforded the title compound (300 mg) as a solid.

$^1$H NMR (DMSO-$d_6$) δ 10.2 (br s, 1H), 8.00 (m, 1H), 7.28 (m, 5H), 7.02 (m, 3H), 6.45 (br s, 1H), 4.15 (d, 1H), 4.05 (m, 1H), 3.55 (d, 1H).

SYNTHESIS EXAMPLE 3

Preparation of N-(2-chlorophenyl)-2-oxo-4-[4-(trifluoromethyl)phenyl]-3-piperidinecarboxamide (Compound 13)

Using the method of Example 1, 2-oxo-4-[4-(trifluoromethyl)phenyl]-3-piperidinecarboxylic acid and 2-chloroaniline afforded the title compound (220 mg) as a solid.

$^1$H NMR δ 9.6 (br s, 1H), 7.9 (br s, 1H), 7.7 (d, 2H), 7.6-7.5 (m, 3H), 7.4 (d, 1H), 7.3 (t, 1H), 7.1 (t, 1H), 3.9 (d, 1H), 3.6-3.5 (m, 1H), 3.4-3.2 (m, 2H), 2.0-1.9 (m, 2H).

SYNTHESIS EXAMPLE 4

Preparation of (3S,4S)-4-(4-fluorophenyl)-1-methyl-2-oxo-N-[2-(trifluoromethyl)phenyl]-3-piperidinecarboxamide (Compound 53)

Step A: Preparation of 1,3-bis(phenylmethyl)-2-[(1S)-1-(4-fluorophenyl)-3-oxopropyl]propanedioate To a solution of trans-4-fluorocinnamaldehyde (14.57 g, 97.07 mmol) in ethanol (150 mL) was added (R)-Jorgensen catalyst (i.e. (R)-α,α-Bis[3,5-bis(trifluoromethyl)phenyl]-2-pyrrolidinemethanol trimethylsilyl ether) (2.9 g, 4.86 mmol) and dibenzyl malonate (13.8 g 48.53 mmol) at 0° C. The resulting mixture was stirred at 0° C. for 100 h. Upon completion, the reaction mixture was concentrated under reduced pressure and the residue was poured into water (300 mL) and extracted with ethyl acetate (3×200 mL). The combined organic layers were washed with water, followed by brine solution, and dried over anhydrous $Na_2SO_4$. The mixture was filtered and concentrated under reduced pressure to afford a crude residue. The resulting residue was then purified by column chromatography eluting with ethyl acetate in petroleum ether (1:4) to afford the title compound (12.0 g) as off-white solid.

MS=433.10 (M−1); $[α]^{23}D$=+16.07.

Step B: Preparation of phenylmethyl (3R,4S)-4-(4-fluorophenyl)-1-methyl-2-oxo-3-piperidinecarboxylate To a solution of 1,3-bis(phenylmethyl)-2-[(1S)-1-(4-fluorophenyl)-3-oxopropyl]propanedioate (i.e. the product of Step A, 7.0 g, 16.12 mmol) in 1,4-dioxane (70 mL) was added 2 M solution of methylamine in tetrahydrofuran (24.2 mL, 48.37 mmol) and the resulting mixture was stirred at ambient temperature for 15 min. To this mixture was then added sodium triacetoxyborohydride (4.43 g, 20.9 mmol) at ambient temperature, and the resulting mixture was stirred at room temperature for 16 h. The reaction mixture was concentrated under reduced pressure to obtain a crude residue, which was diluted with ethyl acetate (200 mL) and was washed with saturated sodium bicarbonate solution (100 mL) followed by washing with water. The organic layers were combined and dried over anhydrous $Na_2SO_4$, filtered, then concentrated under reduced pressure to afford a crude residue. Purification was accomplished by preparative HPLC to afford the title compound (1.0 g) as an off-white solid.

MS=342.20 (M+1).

Step C: Preparation of (3R,4S)-4-(4-fluorophenyl)-1-methyl-2-oxo-3-piperidinecarboxylic acid To a solution of (3R,4S)-4-(4-fluorophenyl)-1-methyl-2-oxo-3-piperidinecarboxylate (i.e. the product of Step B, 1.0 g, 3.6 mmol) in tetrahydrofuran (10 mL) and water (10 mL) was added lithium hydroxide monohydrate (0.614 g, 17.92 mmol) and the resulting mixture was stirred at ambient temperature for 16 h. The reaction mixture was concentrated under reduced pressure, and the resulting residue was diluted with ethyl acetate (100 mL) and washed with water (50 mL). The organic layer was discarded and the aqueous layer was acidified with 1 N aqueous hydrochloric acid and extracted with ethyl acetate (3×30 mL). The combined organic layers were washed with water, brine solution, then dried over anhydrous $Na_2SO_4$ and filtered. Concentration of the filtrate under reduced pressure afforded a crude residue. The crude residue was purified by washing with diethyl ether to afford the title compound (0.5 g) as an off-white solid.

MS=252.21 (M+1).

Step D: Preparation of (3S,4S)-4-(4-fluorophenyl)-1-methyl-2-oxo-N-[2-(trifluoromethyl)phenyl]-3-piperidinecarboxamide To a solution of (3R,4S)-4-(4-fluorophenyl)-1-methyl-2-oxo-3-piperidinecarboxylic acid (i.e. the product of Step C, 0.2 g, 0.8 mmol) in dichloromethane (10 mL) was added 2-(trifluoromethyl)aniline (0.153 g, 0.95 mmol), propylphosphonic anhydride (50% solution in ethyl acetate, 1 mL, 1.6 mmol), triethylamine (0.35 mL, 3.0 mmol) and the resulting mixture stirred at room temperature for 16 h. The reaction mixture was diluted with dichloromethane (50 mL) and washed with water (20 mL). The organic layer was separated, dried over anhydrous $Na_2SO_4$, filtered, and concentrated under reduced pressure to afford a crude residue. This residue was then purified by column chromatography eluting with ethyl acetate in petroleum ether (1:5) to afford the title compound as an off-white solid.

$^1$H NMR (400 MHz, CDCl$_3$): δ 9.48 (br s, 1H), 8.13 (d, 1H), 7.59 (d, 1H), 7.51 (t, 1H), 7.17-7.23 (m, 3H), 7.02 (t, 2H), 3.98 (t, 1H), 3.64 (d, 1H), 3.38 (m, 1H), 3.19 (m, 1H), 3.06 (s, 3H), 2.18 (m, 1H), 1.98 (m, 1H); MS=395.2 (M+1); m.p.=72-74° C.

SYNTHESIS EXAMPLE 5

Preparation of (3R,4S)-4-(4-fluorophenyl)-2-oxo-N-[2-(trifluoromethyl)phenyl]-3-piperidinecarboxamide (Compound 57)

Step A: Preparation of phenylmethyl (3R,4S)-4-(4-fluorophenyl)-1-[(4-methoxyphenyl)methyl]-2-oxo-3-piperidinecarboxylate To a solution of 1,3-bis(phenylmethyl)-2-[(1 S)-1-(4-fluorophenyl)-3-oxopropyl]propanedioate (i.e. the product of Step A in Synthesis Example 4, 3.0 g, 6.91 mmol) in 1,4-dioxane (30 mL) was added 4-methoxybenzylamine (2.70 mL, 20.73 mmol) and the mixture was stirred at room temperature for 15 min. To this mixture was then added sodium triacetoxyborohydride (2.92 g, 13.81 mmol), and the resulting mixture was stirred for 16 h. The reaction mixture was concentrated under reduced pressure to provide a crude residue. This residue was diluted with ethyl acetate (200 mL) and washed with saturated sodium bicarbonate solution (100 mL), followed by water. The layers were separated, and the organic layer was dried over anhydrous Na$_2$SO$_4$, filtered, and concentrated under reduced pressure. The material so obtained was purified by silica gel column chromatography eluting with ethyl acetate in petroleum ether (1:1) to afford the title compound (2.5 g) as a pale yellow liquid.

MS=448.3 (M+1).

Step B: Preparation of (3R,4S)-4-(4-fluorophenyl)-1-[(4-methoxyphenyl)methyl]-2-oxo-3-piperidinecarboxylic acid To a solution of (3R,4S)-4-(4-fluorophenyl)-1-[(4-methoxyphenyl)methyl]-2-oxo-3-piperidinecarboxylate (i.e. the product of Step A, 2.0 g, 4.46 mmol) in tetrahydrofuran (20 mL) and water (20 mL) was added lithium hydroxide monohydrate (0.94 g, 22.34 mmol) and the reaction mixture was stirred at room temperature for 16 h. The reaction mixture was concentrated under reduced pressure, and the resulting residue was diluted with diethyl ether (100 mL) and washed with water (50 mL). The layers were separated and the aqueous layer was acidified with 1 N aqueous hydrochloric acid and extracted with ethyl acetate (3×40 mL). The combined organic layers were washed with water, followed by brine solution, then dried over anhydrous Na$_2$SO$_4$. The mixture was then filtered and concentrated under reduced pressure to afford the title compound (1.5 g) as a pale brown solid.

MS=358.20 (M+1); m.p.=64-67° C.

Step C: Preparation of (3S,4S)-4-(4-fluorophenyl)-1-[(4-methoxyphenyl)methyl]-2-oxo-N-[2-(trifluoromethyl)phenyl]-3-piperidinecarboxamide To a solution of (3R,4S)-4-(4-fluorophenyl)-1-[(4-methoxyphenyl)methyl]-2-oxo-3-piperidinecarboxylic acid (i.e. the product of Step B, 0.8 g, 2.24 mmol) and 2-trifluoromethylaniline (0.43 g, 2.68 mmol) in dichloromethane (10 mL) was added propylphosphonic anhydride (50% solution in ethyl acetate, 2.84 mL, 4.47 mmol), triethylamine (0.9 mL, 6.70 mmol), and the reaction mixture was stirred at ambient temperature for 16 h. The reaction mixture was diluted with dichloromethane (100 mL) and washed with water (50 mL). The organic layer was separated, dried over anhydrous Na$_2$SO$_4$, filtered, and concentrated under reduced pressure to afford a crude residue. This crude material was purified by column chromatography eluting with ethyl acetate in petroleum ether (1:3) to afford the title compound (0.6 g) as a pale green liquid.

MS=501.29 (M+1).

Step D: Preparation of (3R,4S)-4-(4-fluorophenyl)-2-oxo-N-[2-(trifluoromethyl)phenyl]-3-piperidinecarboxamide To (3S,4S)-4-(4-fluorophenyl)-1-[(4-methoxyphenyl)methyl]-2-oxo-N-[2-(trifluoromethyl)phenyl]-3-piperidinecarboxamide (i.e. the product of Step C, 0.5 g, 0.99 mmol) was added trifluoroacetic acid (10 mL) and the reaction mixture was stirred at 110° C. for 72 h. The reaction mixture was concentrated under reduced pressure to remove trifluoroacetic acid. The resulting residue was neutralized with saturated NaHCO$_3$ solution and extracted with dichloromethane (2×100 mL). The combined organic layers were dried over anhydrous Na$_2$SO$_4$, filtered, and concentrated under reduced pressure. The resulting material was purified by silica gel column chromatography eluting with ethyl acetate in petroleum ether (1:3) to afford the title compound as an off-white solid.

$^1$H NMR (400 MHz, DMSO-d$_6$): δ 9.58 (s, 1H), 7.89 (s, 1H), 7.61 (m, 2H), 7.40-7.29 (m, 4H), 7.11 (m, 2H), 3.76 (d, 1H), 3.42 (m, 1H), 3.23 (m, 1H), 2.45 (m, 1H), 1.91 (m, 2H); MS=381.22 (M+1); m.p.=81-84° C.

By the procedures described herein together with methods known in the art, the following compounds of Tables 1 to 56 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, c-Pr cyclopropyl, t-Bu means tertiary butyl, c-Bu means cyclobutyl, Ph means phenyl, OMe means methoxy, OEt means ethoxy, SMe means methylthio, NHMe means methylamino, CN means cyano, NO$_2$ means nitro, TMS means trimethylsilyl, SOMe means methylsulfinyl, and SO$_2$Me means methylsulfonyl.

TABLE 1

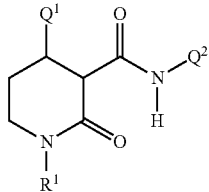

R$^1$ is H; Q$^2$ is Ph(2-F); and Q$^1$ is

| Q$^1$ | Q$^1$ | Q$^1$ |
|---|---|---|
| Ph(3-Cl) | Ph(3-F, 4-OCHF$_2$) | Ph(2-F, 3-F, 4-TMS) |
| Ph(3-F) | Ph(3-F, 4-SO$_2$Me) | Ph(2-F, 3-F, 4-CN) |
| Ph(3-Br) | Ph(3-F, 4-TMS) | Ph(2-F, 3-Br, 4-Cl) |
| Ph(3-Me) | Ph(3-F, 4-CN) | Ph(2-F, 3-Br, 4-F) |
| Ph(3-Et) | Ph(3-Br, 4-Cl) | Ph(2-F, 3-Br, 4-Br) |
| Ph(3-t-Bu) | Ph(3-Br, 4-F) | Ph(2-F, 3-Br, 4-Me) |
| Ph(3-i-Pr) | Ph(3,4-di-Br) | Ph(2-F, 3-Br, 4-t-Bu) |
| Ph(3-c-Pr) | Ph(3-Br, 4-Me) | Ph(2-F, 3-Br, 4-c-Pr) |
| Ph(3-cyclohexyl) | Ph(3-F, 4-t-Bu) | Ph(2-F, 3-Br, 4-CF$_3$) |
| Ph(3-CH=CH$_2$) | Ph(3-Br, 4-c-Pr) | Ph(2-F, 3-Br, 4-CHF$_2$) |
| Ph(3-CF$_3$) | Ph(3-Br, 4-CF$_3$) | Ph(2-F, 3-Br, 4-OCF$_3$) |
| Ph(3-CH$_2$CF$_3$) | Ph(3-Br, 4-CHF$_2$) | Ph(2-F, 3-Br, 4-OCHF$_2$) |
| Ph(3-CHF$_2$) | Ph(3-Br, 4-OCF$_3$) | Ph(2-F, 3-Br, 4-SO$_2$Me) |
| Ph(3-CH$_2$F) | Ph(3-Br, 4-OCHF$_2$) | Ph(2-F, 3-Br, 4-TMS) |
| Ph(3-OCF$_3$) | Ph(3-Br, 4-SO$_2$Me) | Ph(2-F, 3-Br, 4-CN) |
| Ph(3-OCH$_2$F) | Ph(3-Br, 4-TMS) | Ph(2-F, 3-Me, 4-Cl) |
| Ph(3-SCF$_3$) | Ph(3-Br, 4-CN) | Ph(2-F, 3-Me, 4-F) |
| Ph(3-SMe) | Ph(3-Me, 4-Cl) | Ph(2-F, 3-Me, 4-Br) |
| Ph(3-SOMe) | Ph(3-Me, 4-F) | Ph(2-F, 3-Me, 4-CF$_3$) |
| 3-SO$_2$Me | Ph(3-Me, 4-Br) | Ph(2-F, 3-Me, 4-t-Bu) |
| Ph(3-OSO$_2$Me) | Ph(3,4-di-Me) | Ph(2-F, 3-Me, 4-t-Bu) |
| Ph(3-C≡CH) | Ph(3-Me, 4-t-Bu) | Ph(2-F, 3-Me, 4-CF$_3$) |
| Ph(3-OMe) | Ph(3-Me, 4-c-Pr) | Ph(2-F, 3-Me, 4-CHF$_2$) |
| Ph(3-OEt) | Ph(3-Me, 4-CF$_3$) | Ph(2-F, 3-Me, 4-OCF$_3$) |
| Ph(3-NHCO$_2$-t-Bu) | Ph(3-Br, 4-CHF$_2$) | Ph(2-F, 3-Me, 4-OCHF$_2$) |
| Ph(3-NHCOMe) | Ph(3-Me, 4-OCF$_3$) | Ph(2-F, 3-Me, 4-SO$_2$Me) |
| Ph(3-NHCOCF$_3$) | Ph(3-Me, 4-OCHF$_2$) | Ph(2-F, 3-Me, 4-TMS) |
| Ph(3-CN) | Ph(3-Me, 4-SO$_2$Me) | Ph(2-F, 3-Me, 4-CN) |
| Ph(3-NO$_2$) | Ph(3-Me, 4-TMS) | Ph(2-F, 3-t-Bu, 4-Cl) |
| Ph(3-Ph) | Ph(3-Me, 4-CN) | Ph(2-F, 3-t-Bu, 4-F) |
| Ph(3-COMe) | Ph(3-t-Bu, 4-Cl) | Ph(2-F, 3-t-Bu, 4-Br) |
| Ph(3-OCOMe) | Ph(3-t-Bu, 4-F) | Ph(2-F, 3-t-Bu, 4-Me) |
| Ph(3-CO$_2$Me) | Ph(3-t-Bu, 4-Br) | Ph(2-F, 3-t-Bu, 4-t-Bu) |
| Ph(3-OCO$_2$Me) | Ph(3-t-Bu, 4-Me) | Ph(2-F, 3-t-Bu, 4-c-Pr) |
| Ph(3-TMS) | Ph(3,4-di-t-Bu) | Ph(2-F, 3-t-Bu, 4-CF$_3$) |
| Ph(3-Ph) | Ph(3-t-Bu, 4-c-Pr) | Ph(2-F, 3-t-Bu, 4-CHF$_2$) |
| Ph[3-(1H-pyrazol-1-yl)] | Ph(3-t-Bu, 4-CF$_3$) | Ph(2-F, 3-t-Bu, 4-OCF$_3$) |
| Ph[(3-(2H-1,2,3-triazol-2-yl)] | Ph(3-t-Bu, 4-CHF$_2$) | Ph(2-F, 3-t-Bu, 4-OCHF$_2$) |
| Ph[3-(1H-imidazol-1-yl)] | Ph(3-t-Bu, 4-OCF$_3$) | Ph(2-F, 3-t-Bu, 4-SO$_2$Me) |
| Ph[3-(3-pyridinyl)] | Ph(3-t-Bu, 4-OCHF$_2$) | Ph(2-F, 3-t-Bu, 4-TMS) |
| Ph[3-(4-pyridinyl)] | Ph(3-t-Bu, 4-SO$_2$Me) | Ph(2-F, 3-t-Bu, 4-CN) |
| Ph[3-(2-pyridinyl)] | Ph(3-t-Bu, 4-TMS) | Ph(2-F, 3-c-Pr, 4-F) |
| 4-Pyridinyl(2-CF$_3$) | Ph(3-t-Bu, 4-CN) | Ph(2-F, 3-c-Pr, 4-Br) |
| 4-Pyridinyl(2-Cl) | Ph(3-c-Pr, 4-Cl) | Ph(2-F, 3-c-Pr, 4-Me) |
| 4-Pyridinyl(2-F) | Ph(3-c-Pr, 4-F) | Ph(2-F, 3-c-Pr, 4-t-Bu) |
| 4-Pyridinyl(2-OCF$_3$) | Ph(3-c-Pr, 4-Br) | Ph(2-F, 3,4-di-c-Pr) |
| 4-Pyridinyl(2-Me) | Ph(3-c-Pr, 4-Me) | Ph(2-F, 3-c-Pr, 4-CF$_3$) |
| 4-Pyridinyl(2-Br) | Ph(3-c-Pr, 4-t-Bu) | Ph(2-F, 3-c-Pr, 4-CHF$_2$ |
| 4-Pyridinyl | Ph(3,4-di-c-Pr) | Ph(2-F, 3-c-Pr, 4-OCF$_3$) |
| 1H-Pyrazol-4-yl(1-Me) | Ph(3-c-Pr, 4-CF$_3$) | Ph(2-F, 3-c-Pr, 4-OCHF$_2$) |
| 1H-Pyrazol-4-yl(1-CH$_2$CF$_3$) | Ph(3-c-Pr, 4-CHF$_2$) | Ph(2-F, 3-c-Pr, 4-SO$_2$Me) |
| 1H-Imidazol-2-yl(1-Me) | Ph(3-c-Pr, 4-OCF$_3$) | Ph(2-F, 3-c-Pr, 4-TMS) |
| 1H-Imidazol-2-yl(1-CH$_2$CF$_3$) | Ph(3-c-Pr, 4-OCHF$_2$) | Ph(2-F, 3-c-Pr, 4-CN) |
| 1H-Imidazol-2-yl(1-Me, 5-Cl) | Ph(3-c-Pr, 4-SO$_2$Me) | |

TABLE 1-continued

| | | |
|---|---|---|
| 1H-Imidazol-2-yl(1-Me, 5-F) | Ph(3-c-Pr, 4-TMS) | Ph(2-F, 3-CF$_3$, 4-Cl) |
| 2-Thienyl | Ph(3-c-Pr, 4-CN) | Ph(2-F, 3-CF$_3$, 4-F) |
| 2-Thienyl(4-F) | Ph(3-CF$_3$, 4-Cl) | Ph(2-F, 3-CF$_3$, 4-Br) |
| 2-Thienyl(4-Cl) | Ph(3-CF$_3$, 4-F) | Ph(2-F, 3-CF$_3$, 4-Me) |
| 2-Thienyl(4-CF$_3$) | Ph(3-CF$_3$, 4-Br) | Ph(2-F, 3-CF$_3$, 4-t-Bu) |
| 2-Thienyl(5-F) | Ph(3-CF$_3$, 4-Me) | Ph(2-F, 3-CF$_3$, 4-c-Pr) |
| 2-Thienyl(5-Cl) | Ph(3-CF$_3$, 4-t-Bu) | Ph(2-F, 3-CF$_3$, 4-CF$_3$) |
| 2-Thienyl(5-CF$_3$) | Ph(3-CF$_3$, 4-c-Pr) | Ph(2-F, 3-CF$_3$, 4-CHF$_2$) |
| Ph(4-Cl) | Ph(3,4-di-CF$_3$) | Ph(2-F, 3-CF$_3$, 4-OCF$_3$) |
| Ph(4-F) | Ph(3-CF$_3$, 4-CHF$_2$) | Ph(2-F, 3-CF$_3$, 4-OCHF$_2$) |
| Ph(4-Br) | Ph(3-CF$_3$, 4-OCF$_3$) | Ph(2-F, 3-CF$_3$, 4-SO$_2$Me) |
| Ph(4-Me) | Ph(3-CF$_3$, 4-OCHF$_2$) | Ph(2-F, 3-CF$_3$, 4-TMS) |
| Ph(4-Et) | Ph(3-CF$_3$, 4-SO$_2$Me) | Ph(2-F, 3-CF$_3$, 4-CN) |
| Ph(4-t-Bu) | Ph(3-CF$_3$, 4-TMS) | Ph(2-F, 3-OCF$_3$, 4-Cl) |
| Ph(4-i-Pr) | Ph(3-CF$_3$, 4-CN) | Ph(2-F, 3-OCF$_3$, 4-Br) |
| Ph(4-c-Pr) | Ph(3-OCF$_3$, 4-Cl) | Ph(2-F, 3-OCF$_3$, 4-Me) |
| Ph(4-cyclohexyl) | Ph(3-OCF$_3$, 4-F) | Ph(2-F, 3-OCF$_3$, 4-t-Bu) |
| Ph(4-CH=CH$_2$) | Ph(3-OCF$_3$, 4-Br) | Ph(2-F, 3-OCF$_3$, 4-c-Pr) |
| Ph(4-CF$_3$) | Ph(3-OCF$_3$, 4-Me) | Ph(2-F, 3-OCF$_3$, 4-CF$_3$) |
| Ph(4-CH$_2$CF$_3$) | Ph(3-OCF$_3$, 4-t-Bu) | Ph(2-F, 3-OCF$_3$, 4-CHF$_2$) |
| Ph(4-CHF$_2$) | Ph(3-OCF$_3$, 4-c-Pr) | Ph(2-F, 3-OCF$_3$, 4-OCF$_3$) |
| Ph(4-CH$_2$F) | Ph(3-OCF$_3$, 4-CF$_3$) | Ph(2-F, 3-OCF$_3$, 4-OCHF$_2$) |
| Ph(4-OCF$_3$) | Ph(3-OCF$_3$, 4-CHF$_2$) | Ph(2-F, 3-OCF$_3$, 4-SO$_2$Me) |
| Ph(4-OCH$_2$F) | Ph(3,4-di-OCF$_3$) | Ph(2-F, 3-OCF$_3$, 4-TMS) |
| Ph(4-SCF$_3$) | Ph(3-OCF$_3$, 4-OCHF$_2$) | Ph(2-F, 3-OCF$_3$, 4-CN) |
| Ph(4-SMe) | Ph(3-OCF$_3$, 4-SO$_2$Me) | Ph(2-F, 3-OCF$_3$, 4-Cl) |
| Ph(4-SOMe) | Ph(3-OCF$_3$, 4-TMS) | Ph(2-F, 3-OCF$_3$, 4-F) |
| 4-SO$_2$Me | Ph(3-OCF$_3$, 4-CN) | Ph(2-F, 3-OCF$_3$, 4-Br) |
| Ph(4-OSO$_2$Me) | Ph(3-SO$_2$Me, 4-Cl) | Ph(2-F, 3-OCF$_3$, 4-Me) |
| Ph(4-C≡CH) | Ph(3-SO$_2$Me, 4-F) | Ph(2-F, 3-OCF$_3$, 4-t-Bu) |
| Ph(4-OMe) | Ph(3-SO$_2$Me, 4-Br) | Ph(2-F, 3-OCF$_3$, 4-c-Pr) |
| Ph(4-OEt) | Ph(3-SO$_2$Me, 4-Me) | Ph(2-F, 3-OCF$_3$, 4-CF$_3$) |
| Ph(4-NHCO$_2$-t-Bu) | Ph(3-SO$_2$Me, 4-t-Bu) | Ph(2-F, 3-OCF$_3$, 4-CHF$_2$) |
| Ph(4-NHCOMe) | Ph(3-SO$_2$Me, 4-c-Pr) | Ph(2-F, 3-SO$_2$Me, 4-CHF$_2$) |
| Ph(4-NHCOCF$_3$) | Ph(3-SO$_2$Me, 4-CF$_3$) | Ph(2-F, 3-SO$_2$Me, 4-OCF$_3$) |
| Ph(4-CN) | Ph(3-SO$_2$Me, 4-CHF$_2$) | Ph(2-F, 3-SO$_2$Me, 4-OCHF$_2$) |
| Ph(4-NO$_2$) | Ph(3-SO$_2$Me, 4-OCF$_3$) | Ph(2-F, 3,4-di-SO$_2$Me) |
| Ph(4-Ph) | Ph(3-SO$_2$Me, 4-OCHF$_2$) | Ph(2-F, 3-SO$_2$Me, 4-TMS) |
| Ph(4-COMe) | Ph(3,4-di-SO$_2$Me) | Ph(2-F, 3-SO$_2$Me, 4-CN) |
| Ph(4-OCOMe) | Ph(3-SO$_2$Me, 4-TMS) | Ph(2-F, 3-CHF$_2$, 4-Cl) |
| Ph(4-CO$_2$Me) | Ph(3-SO$_2$Me, 4-CN) | Ph(2-F, 3-CHF$_2$, 4-Br) |
| Ph(4-OCO$_2$Me) | Ph(3-CHF$_2$, 4-Cl) | Ph(2-F, 3-CHF$_2$, 4-Me) |
| Ph(4-TMS) | Ph(3-CHF$_2$, 4-F) | Ph(2-F, 3-CHF$_2$, 4-t-Bu) |
| Ph(4-Ph) | Ph(3-CHF$_2$, 4-Br) | Ph(2-F, 3-CHF$_2$, 4-c-Pr) |
| Ph(1H-pyrazol-1-yl) | Ph(3-CHF$_2$, 4-Me) | Ph(2-F, 3-CHF$_2$, 4-CF$_3$) |
| Ph(2H-1,2,3-triazol-2-yl) | Ph(3-CHF$_2$, 4-t-Bu) | |
| Ph(1H-imidazol-1-yl) | Ph(3-CHF$_2$, 4-c-Pr) | Ph(2-F, 3-CHF$_2$, 4-CHF$_2$) |
| Ph[4-(3-pyridinyl)] | Ph(3-CHF$_2$, 4-CF$_3$) | Ph(2-F, 3-CHF$_2$, 4-OCF$_3$) |
| Ph[4-(4-pyridinyl)] | Ph(3-CHF$_2$, 4-CHF$_2$) | Ph(2-F, 3-CHF$_2$, 4-OCHF$_2$) |
| Ph[4-(2-pyridinyl)] | Ph(3-CHF$_2$, 4-OCF$_3$) | Ph(2-F, 3-CHF$_2$, 4-SO$_2$Me) |
| 3-Pyridinyl(5-CF$_3$) | Ph(3-CHF$_2$, 4-OCHF$_2$) | Ph(2-F, 3-CHF$_2$, 4-TMS) |
| 3-Pyridinyl(5-Cl) | Ph(3-CHF$_2$, 4-SO$_2$Me) | Ph(2-F, 3-CHF$_2$, 4-CN) |
| 3-Pyridinyl(5-F) | Ph(3-CHF$_2$, 4-TMS) | Ph(2-F, 3-CN, 4-Cl) |
| 3-Pyridinyl(5-OCF$_3$) | Ph(3-CHF$_2$, 4-CN) | Ph(2-F, 3-CN, 4-F) |
| 3-Pyridinyl(5-Me) | Ph(3-CN, 4-Cl) | Ph(2-F, 3-CN, 4-Br) |
| 3-Pyridinyl(5-Br) | Ph(3-CN, 4-F) | Ph(2-F, 3-CN, 4-Me) |
| 3-Pyridinyl | Ph(3-CN, 4-Br) | Ph(2-F, 3-CN, 4-t-Bu) |
| 1H-Pyrazol-3-yl(1-Me) | Ph(3-CN, 4-Me) | Ph(2-F, 3-CN, 4-c-Pr) |

TABLE 1-continued

| | | |
|---|---|---|
| 1H-Pyrazol-3-yl(1-CH₂CF₃) | Ph(3-CN, 4-t-Bu) | Ph(2-F, 3-CN, 4-CF₃) |
| 1H-Pyrazol-3-yl(1-Me, 4-F) | Ph(3-CN, 4-c-Pr) | Ph(2-F, 3-CN, 4-CHF₂) |
| 1H-Pyrazol-3-yl(1-Me, 4-Cl) | Ph(3-CN, 4-CF₃) | Ph(2-F, 3-CN, 4-OCF₃) |
| 1H-Imidazol-5-yl(1-Me) | Ph(3-CN, 4-CHF₂) | Ph(2-F, 3-CN, 4-OCHF₂) |
| 1H-Imidazol-5-yl(1-CH₂CF₃) | Ph(3-CN, 4-OCF₃) | Ph(2-F, 3-CN, 4-SO₂Me) |
| 1H-Imidazol-4-yl(1-Me) | Ph(3-CN, 4-OCHF₂) | Ph(2-F, 3-CN, 4-TMS) |
| 1H-Imidazol-4-yl(1-CH₂CF₃) | Ph(3-CN, 4-SO₂Me) | Ph(2-F, 3-CN, 4-CN) |
| 3-Thienyl | Ph(3-CN, 4-TMS) | Ph(2-F, 4-Cl) |
| 3-Thienyl(5-F) | Ph(3,4-di-CN) | Ph(2-F, 4-F) |
| 3-Thienyl(5-Cl) | Ph(2-F, 3-Cl, 4-Cl) | Ph(2-F, 4-Br) |
| 3-Thienyl(5-CF₃) | Ph(2-F, 3-Cl, 4-F) | Ph(2-F, 4-Me) |
| Ph(3,4-di-Cl) | Ph(2-F, 3-Cl, 4-Br) | Ph(2-F, 4-t-Bu) |
| Ph(3-Cl, 4-F) | Ph(2-F, 3-Cl, 4-Me) | Ph(2-F, 4-c-Pr) |
| Ph(3-Cl, 4-Br) | Ph(2-F, 3-Cl, 4-t-Bu) | Ph(2-F, 4-CF₃) |
| Ph(3-Cl, 4-Me) | Ph(2-F, 3-Cl, 4-c-Pr) | Ph(2-F, 4-CHF₂) |
| Ph(3-Cl, 4-t-Bu) | Ph(2-F, 3-Cl, 4-CF₃) | Ph(2-F, 4-OCF₃) |
| Ph(3-Cl, 4-c-Pr) | Ph(2-F, 3-Cl, 4-CHF₂) | Ph(2-F, 4-OCHF₂) |
| Ph(3-Cl, 4-CF₃) | Ph(2-F, 3-Cl, 4-OCF₃) | Ph(2-F, 4-SO₂Me) |
| Ph(3-Cl, 4-CHF₃) | Ph(2-F, 3-Cl, 4-OCHF₂) | Ph(2-F, 4-TMS) |
| Ph(3-Cl, 4-OCF₃) | Ph(2-F, 3-Cl, 4-SO₂Me) | Ph(2-F, 4-CN) |
| Ph(3-Cl, 4-OCHF₂) | Ph(2-F, 3-Cl, 4-TMS) | Ph(2-F, 3-Cl) |
| Ph(3-Cl, 4-SO₂Me) | Ph(2-F, 3-Cl, 4-CN) | Ph(2-F, 3-F) |
| Ph(3-Cl, 4-TMS) | Ph(2-F, 3-F, 4-Cl) | Ph(2-F, 3-Br) |
| Ph(3-Cl, 4-CN) | Ph(2-F, 3-F, 4-F) | Ph(2-F, 3-Me) |
| Ph(3-F, 4-Cl) | Ph(2-F, 3-F, 4-Br) | Ph(2-F, 3-t-Bu) |
| Ph(3,3-di-F) | Ph(2-F, 3-F, 4-Me) | Ph(2-F, 3-c-Pr) |
| Ph(3-F, 4-Br) | Ph(2-F, 3-F, 4-t-Bu) | Ph(2-F, 3-CF₃) |
| Ph(3-F, 4-Me) | Ph(2-F, 3-F, 4-c-Pr) | Ph(2-F, 3-CHF₂) |
| Ph(3-F, 4-t-Bu) | Ph(2-F, 3-F, 4-CF₃) | Ph(2-F, 3-OCF₃) |
| Ph(3-F, 4-c-Pr) | Ph(2-F, 3-F, 4-CHF₂) | Ph(2-F, 3-OCHF₂) |
| Ph(3-F, 4-CF₃) | Ph(2-F, 3-F, 4-OCF₃) | Ph(2-F, 3-SO₂Me) |
| Ph(3-F, 4-CHF₂) | Ph(2-F, 3-F, 4-OCHF₂) | Ph(2-F, 3-TMS) |
| Ph(3-F, 4-OCF₃) | Ph(2-F, 3-F, 4-SO₂Me) | Ph(2-F, 3-CN) |

| Q¹ | Q¹ |
|---|---|
| 1H-Imidazol-2-yl(1-CH₂CF₃, 5-Cl) | 1,3-Benzodioxol-4-yl(2,2-di-F) |
| 1H-Imidazol-2-yl(1-CH₂CF₃, 5-F) | 1H-Pyrazol-3-yl(1-CH₂CF₃, 4-F) |
| 1H-Imidazol-2-yl(1-Me, 5-CF₃) | 1H-Pyrazol-3-yl(1-CH₂CF₃, 4-Cl) |
| 1H-Imidazol-2-yl(1-CH₂CF₃, 5-CF₃) | |

Table 2 is constructed in the same manner except that the Row Heading "R¹ is H; Q² is Ph(2-F); and Q¹ is" is replaced with the Row Heading listed for Table 2 below (i.e. "R¹ is H; Q² is Ph(2,3-F); and Q¹ is"). Therefore the first entry in Table 2 is a compound of Formula 1 wherein R¹ is H; Q² is Ph(2,3-di-F); and Q¹ is Ph(3-Cl) (i.e. 3-chlorophenyl). Tables 3 through 56 are constructed similarly.

| Table | Row Heading |
|---|---|
| 2 | R¹ is H; Q² is Ph(2,3-di-F); and Q¹ is |
| 3 | R¹ is H; Q² is Ph(2-CF₃); and Q¹ is |
| 4 | R¹ is H; Q² is Ph(2-NO₂); and Q¹ is |
| 5 | R¹ is H; Q² is Ph(2-SO₂Me); and Q¹ is |
| 6 | R¹ is H; Q² is Ph(2-Me); and Q¹ is |
| 7 | R¹ is H; Q² is Ph(2-OCF₃); and Q¹ is |
| 8 | R¹ is H; Q² is Ph(2,4-di-F); and Q¹ is |
| 9 | R¹ is H; Q² is 2-Pyridinyl; and Q¹ is |
| 10 | R¹ is H; Q² is Ph(2-Cl); and Q¹ is |
| 11 | R¹ is H; Q² is Ph(2-Br); and Q¹ is |
| 12 | R¹ is H; Q² is Ph(2-Cl,3-F); and Q¹ is |
| 13 | R¹ is H; Q² is Ph(3-Cl,2-F); and Q¹ is |
| 14 | R¹ is H; Q² is Ph(2,3,4-tri-F); and Q¹ is |
| 15 | R¹ is Me; Q² is Ph(2-F); and Q¹ is |
| 16 | R¹ is Me; Q² is Ph(2,3-di-F); and Q¹ is |
| 17 | R¹ is Me; Q² is Ph(2-CF₃); and Q¹ is |
| 18 | R¹ is Me; Q² is Ph(2-NO₂); and Q¹ is |
| 19 | R¹ is Me; Q² is Ph(2-SO₂Me); and Q¹ is |
| 20 | R¹ is Me; Q² is Ph(2-Me); and Q¹ is |
| 21 | R¹ is Me; Q² is Ph(2-OCF₃); and Q¹ is |
| 22 | R¹ is Me; Q² is Ph(2,4-di-F); and Q¹ is |
| 23 | R¹ is Me; Q² is 2-Pyridinyl; and Q¹ is |
| 24 | R¹ is Me; Q² is Ph(2-Cl); and Q¹ is |
| 25 | R¹ is Me; Q² is Ph(2-Br); and Q¹ is |
| 26 | R¹ is Me; Q² is Ph(2-Cl,3-F); and Q¹ is |
| 27 | R¹ is Me; Q² is Ph(3-Cl,2-F); and Q¹ is |
| 28 | R¹ is Me; Q² is Ph(2,3,4-tri-F); and Q¹ is |
| 29 | R¹ is Et; Q² is Ph(2-F); and Q¹ is |
| 30 | R¹ is Et; Q² is Ph(2,3-di-F); and Q¹ is |
| 31 | R¹ is Et; Q² is Ph(2-CF₃); and Q¹ is |
| 32 | R¹ is Et; Q² is Ph(2-NO₂); and Q¹ is |
| 33 | R¹ is Et; Q² is Ph(2-SO₂Me); and Q¹ is |
| 34 | R¹ is Et; Q² is Ph(2-Me); and Q¹ is |
| 35 | R¹ is Et; Q² is Ph(2-OCF₃); and Q¹ is |
| 36 | R¹ is Et; Q² is Ph(2,4-di-F); and Q¹ is |
| 37 | R¹ is Et; Q² is 2-Pyridinyl; and Q¹ is |
| 38 | R¹ is Et; Q² is Ph(2-Cl); and Q¹ is |
| 39 | R¹ is Et; Q² is Ph(2-Br); and Q¹ is |
| 40 | R¹ is Et; Q² is Ph(2-Cl,3-F); and Q¹ is |
| 41 | R¹ is Et; Q² is Ph(3-Cl,2-F); and Q¹ is |
| 42 | R¹ is Et; Q² is Ph(2,3,4-tri-F); and Q¹ is |
| 43 | R¹ is —CH₂OCH₃; Q² is Ph(2-F); and Q¹ is |
| 44 | R¹ is —CH₂OCH₃; Q² is Ph(2,3-di-F); and Q¹ is |
| 45 | R¹ is —CH₂OCH₃; Q² is Ph(2-CF₃); and Q¹ is |
| 46 | R¹ is —CH₂OCH₃; Q² is Ph(2-NO₂); and Q¹ is |
| 47 | R¹ is —CH₂OCH₃; Q² is Ph(2-SO₂Me); and Q¹ is |
| 48 | R¹ is —CH₂OCH₃; Q² is Ph(2-Me); and Q¹ is |
| 49 | R¹ is —CH₂OCH₃; Q² is Ph(2-OCF₃); and Q¹ is |
| 50 | R¹ is —CH₂OCH₃; Q² is Ph(2,4-di-F); and Q¹ is |
| 51 | R¹ is —CH₂OCH₃; Q² is 2-Pyridinyl; and Q¹ is |
| 52 | R¹ is —CH₂OCH₃; Q² is Ph(2-Cl); and Q¹ is |
| 53 | R¹ is —CH₂OCH₃; Q² is Ph(2-Br); and Q¹ is |
| 54 | R¹ is —CH₂OCH₃; Q² is Ph(2-Cl,3-F); and Q¹ is |
| 55 | R¹ is —CH₂OCH₃; Q² is Ph(3-Cl,2-F); and Q¹ is |
| 56 | R¹ is —CH₂OCH₃; Q² is Ph(2,3,4-tri-F); and Q¹ is |

Formulation/Utility

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Tables A-C. Without further elaboration, it is believed that one skilled in the art using the preceding description can utilize the present invention to its fullest extent. The following non-limiting Examples are illustrative of the invention. Percentages are by weight except where otherwise indicated.

EXAMPLE A

| High Strength Concentrate | |
|---|---|
| Compound 9 | 98.5% |
| silica aerogel | 0.5% |
| synthetic amorphous fine silica | 1.0% |

EXAMPLE B

| Wettable Powder | |
|---|---|
| Compound 9 | 65.0% |
| dodecylphenol polyethylene glycol ether | 2.0% |
| sodium ligninsulfonate | 4.0% |

-continued

| Wettable Powder | |
|---|---|
| sodium silicoaluminate | 6.0% |
| montmorillonite (calcined) | 23.0% |

EXAMPLE C

| Granule | |
|---|---|
| Compound 9 | 10.0% |
| attapulgite granules (low volatile matter, 0.71/0.30 mm; U.S.S. No. 25-50 sieves) | 90.0% |

EXAMPLE D

| Extruded Pellet | |
|---|---|
| Compound 9 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

| Emulsifiable Concentrate | |
|---|---|
| Compound 9 | 10.0% |
| polyoxyethylene sorbitol hexoleate $C_6$-$C_{10}$ | 20.0% |
| fatty acid methyl ester | 70.0% |

EXAMPLE F

| Microemulsion | |
|---|---|
| Compound 9 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

| Suspension Concentrate | |
|---|---|
| Compound 9 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

EXAMPLE H

| Emulsion in Water | |
|---|---|
| Compound 9 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

EXAMPLE I

| Oil Dispersion | |
|---|---|
| Compound 9 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 9" is replaced with "Compound 1", "Compound 2", "Compound 3", "Compound 4", "Compound 5", "Compound 6", "Compound 7", "Compound 8", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35", "Compound 36", "Compound 37", "Compound 38", "Compound 39", "Compound 40", "Compound 41", "Compound 42", "Compound 43", "Compound 44", "Compound 45", "Compound 46", "Compound 47", "Compound 48", "Compound 49", "Compound 50", "Compound 51", "Compound 52", "Compound 53", "Compound 54", "Compound 55", "Compound 56", "Compound 57", "Compound 58", "Compound 59", "Compound 60", "Compound 61", "Compound 62" or "Compound 63" above.

Test results indicate that the compounds of the present invention are highly active preemergent and/or postemergent herbicides and/or plant growth regulants. The compounds of the invention generally show highest activity for early postemergence weed control (i.e. applied soon after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have (both preemergent and postemergent herbicidal) activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.005 to 20 kg/ha with a preferred range of about 0.01 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant of a part thereof, particularly of the undesired vegetation, and/or to the growth medium in contact with the plant.

Plant varieties and cultivars of the desired vegetation in the locus treated with a compound of the invention can be obtained by conventional propagation and breeding methods of by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that conatin other desirable characteristics. Plants can be genetically modified to exhibit traits of, for example, herbicide tolerance, insect resistance, modified oil profiles or drought tolerance. Useful genetically modified plants containing single gene transformation events or combinations of transformation events are listed in Table 3. Additional information for the genetic modifications listed in Table 3 can be obtained from publicly available databases maintained, for example, by the U.S. Department of Agriculture.

The following abbreviations, T1 through T37, are used in Table 3 for traits. In the following tables "-" means the entry is not available, "tol." means tolerance, "res." means resistance, "herb." means herbicide and "mod." means modified.

| Trait | Description |
|---|---|
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Mod. flower color |
| T11 | ALS Herb. Tol. |
| T12 | Dicamba Tol. |
| T13 | Anti-allergy |
| T14 | Salt tol. |
| T15 | Cold tol. |
| T16 | Imidazolinone herb. tol. |
| T17 | Mod. alpha-amylase |
| T18 | Pollination control |
| T19 | 2,4-D tol. |
| T20 | Increased lysine |
| T21 | Drought tol. |
| T22 | Delayed ripening/senescence |
| T23 | Mod. product quality |
| T24 | High cellulose |
| T25 | Mod. starch/carbohydrate |
| T26 | Insect & disease res. |
| T27 | High tryptophan |
| T28 | Erect leaves semidwarf |
| T29 | Semidwarf |
| T30 | Low iron tol. |
| T31 | Mod. oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Mod. product |

TABLE 3

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |

TABLE 3-continued

| Crop | Event Name | Event Code | Trait(s) | Gene(s) |
|---|---|---|---|---|
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-88302-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T7 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |

TABLE 3-continued

| Crop | Event Name | Event Code | Trait(s) | Gene(s) |
|---|---|---|---|---|
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |

TABLE 3-continued

| Crop | Event Name | Event Code | Trait(s) | Gene(s) |
|---|---|---|---|---|
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Mod. avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); g0xv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, cyclopyrimorate, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butoxyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metamsodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carb onyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione, 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide, and 2-methyl-N-(4-methyl-1,2,5-oxadiazol-3-yl)-3-(methyl sulfinyl)-4-(trifluoromethyl) benzamide.

Other herbicides also include bioherbicides such as *Alternaria destruens* Simmons, *Colletotrichum gloeosporiodes* (Penz.) Penz. & Sacc., *Drechsiera monoceras* (MTB-951),

*Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual,* 13th Edition, C. D. S. Tomlin, Ed., British Crop Protection Council, Farnham, Surrey, U. K., 2003 and *The BioPesticide Manual,* 2nd Edition, L. G. Copping, Ed., British Crop Protection Council, Farnham, Surrey, U. K., 2001.

For embodiments where one or more of these various mixing partners are used, active ingredients are often applied at an application rate between one-half and the full application rate specified on product labels for use of the active ingredient alone. The amounts are listed in references such as *The Pesticide Manual*, and the *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Of note is 2-methoxy-N-[[4-[[(methylamino)carbonyl]amino]phenyl]sulfonyl]-benzamide (alternatively named N-(2-methoxybenzoyl)-4-[(methylaminocarbonyl)amino]benzenesulfonamide; CAS #129531-12-0) mixed with any one of the compounds listed in Index Tables A. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with another herbicide. Table A1 lists particular combinations of Component (a) (i.e. a specific compound of the present invention) with another herbicide as Component (b) illustrative of the mixtures, compositions and methods of the present invention. Compound 17 in the Component (a) column is identified in Index Table A. The second column of Table A1 lists the specific Component (b) compound (e.g., “2,4-D” in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 17 in Index Table A) with 2,4-D is typically applied in a weight ratio between 1:192-6:1. The remaining lines of Table A1 are to be construed similarly.

TABLE A1

| Component (a) (Compound) | Component (b) | Typical Weight Ratio | More Typical Weight Ratio | Most Typical Weight Ratio |
|---|---|---|---|---|
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Cafenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cinosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |

TABLE A1-continued

| Component (a) (Compound) | Component (b) | Typical Weight Ratio | More Typical Weight Ratio | Most Typical Weight Ratio |
|---|---|---|---|---|
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halauxifen | 1:20-56:1 | 1:6-19:1 | 1:2-4:1 |
| 1 | Halauxifen-methyl | 1:20-56:1 | 1:6-19:1 | 1:2-4:1 |
| 1 | Halosulfuron-methyl | 1:17-68:1 | 1:5-23:1 | 1:2-5:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |

TABLE A1-continued

| Component (a) (Compound) | Component (b) | Typical Weight Ratio | More Typical Weight Ratio | Most Typical Weight Ratio |
|---|---|---|---|---|
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencalb | 1:768-2:1 | 1:256-1:2 | 1:96-1:11 |
| 1 | Topramezone | 1:6-168:1 | 1:2-56:1 | 1:1-11:1 |
| 1 | Tralkoxydim | 1:68-17:1 | 1:22-6:1 | 1:8-2:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 1 in the Component (a) column is identified in Index Table A. Thus, for example, in Table A2 the entries below the "Component (a)" column heading all recite "Compound 2" (i.e. Compound 1 identified in Index Table A), and the first line below the column headings in Table A2 specifically discloses a mixture of Compound 2 with 2,4-D. Table A3 is constructed similarly.

| Table Number | Component (a) Column Entries |
|---|---|
| A2 | Compound 2 |
| A3 | Compound 3 |

| Table Number | Component (a) Column Entries |
|---|---|
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |
| A17 | Compound 17 |
| A18 | Compound 18 |
| A19 | Compound 19 |
| A20 | Compound 20 |
| A21 | Compound 21 |
| A22 | Compound 22 |
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |
| A31 | Compound 31 |
| A32 | Compound 32 |
| A33 | Compound 33 |
| A34 | Compound 34 |
| A35 | Compound 35 |
| A36 | Compound 36 |
| A37 | Compound 37 |
| A38 | Compound 38 |
| A39 | Compound 39 |
| A40 | Compound 40 |
| A41 | Compound 41 |
| A42 | Compound 42 |
| A43 | Compound 43 |
| A44 | Compound 44 |
| A45 | Compound 45 |
| A46 | Compound 46 |
| A47 | Compound 47 |
| A48 | Compound 48 |
| A49 | Compound 49 |
| A50 | Compound 50 |
| A51 | Compound 51 |
| A52 | Compound 52 |
| A53 | Compound 53 |
| A54 | Compound 54 |
| A55 | Compound 55 |
| A56 | Compound 56 |
| A57 | Compound 57 |
| A58 | Compound 58 |
| A59 | Compound 59 |
| A60 | Compound 60 |
| A61 | Compound 61 |
| A62 | Compound 62 |
| A63 | Compound 63 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention on specific weeds. The weed control afforded by the compounds is not limited, however, to these species. See Index Table A for compound descriptions. The following abbreviations are used in the Index Tables which follow: Ph is phenyl, PMB is p-methoxybenzyl and "Cmpd. No" stands for "Compound Number. The abbreviation "Ex." stands for "Example and is followed by a number indicating in which example the compound is prepared.

INDEX TABLE A[1]

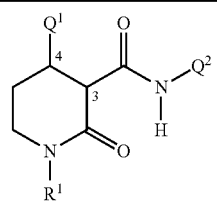

| Cmpd. No. | $Q^1$ | $Q^2$ | $R^1$ | m.p. (° C.) | MS |
|---|---|---|---|---|---|
| 1 | Ph(3,4-di-F) | Ph(2-F) | H | 137-131 | |
| 2 | Ph | Ph(2-CF$_3$) | H | 140-143 | |
| 3 | Ph | Ph(2-F) | H | 143-147 | |
| 4 | Ph(4-F) | Ph(2-CF$_3$) | H | 155-158 | |
| 5 | Ph(4-F) | Ph(2-F) | H | 158-161 | |
| 6 | Ph(3,4-di-F) | Ph(2-CF$_3$) | H | 142-145 | |
| 7 | Ph(2-CF$_3$) | Ph(2-CF$_3$) | H | 195-196 | |
| 8 | Ph(2-CF$_3$) | Ph(2,3-di-F) | H | 178-180 | |
| 9 (Ex. 1) | Ph(3-CF$_3$) | Ph(2,3-di-F) | H | 109-111* | |
| 10 | Ph(3-CF$_3$) | Ph(2-CF$_3$) | H | 292-295 | |
| 11 | Ph(4-CF$_3$) | Ph(2,3-di-F) | H | 180-182 | |
| 12 | Ph(4-CF$_3$) | Ph(2-CF$_3$) | H | 204-207 | |
| 13 (Ex. 3) | Ph(4-CF$_3$) | Ph(2-Cl) | H | 108-112* | |
| 14 (Ex. 2) | Ph(4-CF$_3$) | Ph(2-F) | H | 103-107* | |
| 15 | Ph(4-CF$_3$) | Ph(2-Cl, 3-F) | H | 203-207 | |
| 16 | Ph(3-CF$_3$) | Ph(3-Cl, 2-F) | H | 77-79 | |
| 17 | Ph(3-CF$_3$) | Ph(2-Cl) | H | 70-77 | |
| 19 | Ph(3-CF$_3$) | Ph(2-Cl, 3-F) | H | 68-70 | |
| 20 (3S, 4R) | Ph(3-CF$_3$) | Ph(2,3-di-F) | H | 133-137 | |

INDEX TABLE A[(1)]-continued

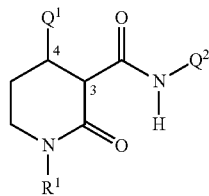

| Cmpd. No. | $Q^1$ | $Q^2$ | $R^1$ | m.p. (° C.) | MS |
|---|---|---|---|---|---|
| 21 (3R, 4S) | Ph(3-CF$_3$) | Ph(2,3-di-F) | H | 136-139 | |
| 22 (3R, 4S) | Ph(4-CF$_3$) | Ph(2,3-di-F) | H | | 399 (M + 1) |
| 23 (3S, 4R) | Ph(4-CF$_3$) | Ph(2,3-di-F) | H | 76-79 | |
| 24 (3S, 4R) | Ph(3-CF$_3$) | Ph(3-Cl, 2-F) | H | 74-77 | |
| 25 (3R, 4S) | Ph(3-CF$_3$) | Ph(3-Cl, 2-F) | H | 81-84 | |
| 26 | Ph(3-CF$_3$) | Ph(2-Me, 3-F) | H | 189-192 | |
| 27 | Ph(3-CF$_3$) | Ph(2,4-di-F) | H | 169-171 | |
| 28 | Ph(3-CF$_3$) | Ph(2,3,4-tri-F) | H | 66-68 | |
| 29 (3S, 4R) | Ph(3-CF$_3$) | Ph(2,3,4-tri-F) | H | 183-187 | |
| 30 (3R, 4S) | Ph(3-CF$_3$) | Ph(2,3,4-tri-F) | H | 183-186 | |
| 31 | Ph(3-CF$_3$) | Ph(2,3-di-Cl) | H | 170-172 | |
| 32 | Ph(3-CF$_3$) | Ph(2-S(O)$_2$Me) | H | 209-211 | |
| 33 | Ph(3-Cl) | Ph(2-CF$_3$) | H | 167-169 | |
| 34 | Ph(3-Cl) | Ph(2-F) | H | 88-90 | |
| 35 | Ph | Ph(2,3-di-F) | H | 190-192 | |
| 36 | Ph(3-Cl) | Ph(2,3-di-F) | H | 100-102 | |
| 37 | Ph(3-OCF$_3$) | Ph(2-F) | H | | 397 (M + 1) |
| 38 | Ph(3-OCF$_3$) | Ph(2-CF$_3$) | H | 141-143 | |
| 39 | Ph(3-OCF$_3$) | Ph(2,3-di-F) | H | 89-91 | |
| 40 (3R, 4S) | Ph(3-OCF$_3$) | Ph(2,3-di-F) | H | | 415 (M + 1) |
| 41 (3S, 4R) | Ph(3-OCF$_3$) | Ph(2,3-di-F) | H | | 415 (M + 1) |
| 42 (3R, 4S) | Ph(3-Cl) | Ph(2,3-di-F) | H | 103-105 | |
| 43 (3S, 4R) | Ph(3-Cl) | Ph(2,3-di-F) | H | 91-93 | |
| 44 | Ph(3-OCHF$_2$) | Ph(2,3,4-tri-F) | H | 150-154 | |
| 45 | Ph(3-OCHF$_2$) | Ph(2-F) | H | 196-200 | |
| 46 | Ph(3-OCHF$_2$) | Ph(2,3-di-F) | H | 173-177 | |
| 47 | Ph(3-CHF$_2$) | Ph(2,3,4-tri-F) | H | 144-147 | |
| 48 | Ph(3-CHF$_2$) | Ph(2-F) | H | 169-172 | |
| 49 | Ph(3-CHF$_2$) | Ph(2,3-di-F) | H | 134-137 | |
| 50 (3S, 4S) | Ph(4-F) | Ph(2-CF$_3$) | c-Pr | | 419 (M + 1) |
| 51 (3S, 4S) | Ph(4-F) | Ph(2-CF$_3$) | —CH$_2$—Ph | | 471 (M + 1) |
| 52 (3S, 4S) | Ph(4-F) | Ph(2,3-di-F) | Me | 128-131 | |
| 53 (3S, 4S) (Ex. 4) | Ph(4-F) | Ph(2-CF$_3$) | Me | 72-74 | |
| 54 (3R, 4S) | Ph(4-CF$_3$) | Ph(2,3,4-tri-F) | H | 85-88 | |
| 55 (3S, 4R) | Ph(4-CF$_3$) | Ph(2,3,4-tri-F) | H | 85-88 | |
| 56 (3S, 4S) | Ph(4-F) | Ph(2-CF$_3$) | PMB | | 501 (M + 1) |
| 57 (3R, 4S) (Ex. 5) | Ph(4-F) | Ph(2-CF$_3$) | H | 81-84 | |
| 58 (3S, 4R) | Ph(3-OCF$_3$) | Ph(3-Cl, 2-F) | H | | 431 (M + 1) |
| 59 (3R, 4S) | Ph(3-OCF$_3$) | Ph(3-Cl, 2-F) | H | 71-74 | |
| 60 (3S, 4R) | Ph(3-OCF$_3$) | Ph(2,3,4-tri-F) | H | | 433 (M + 1) |
| 61 (3R, 4S) | Ph(3-OCF$_3$) | Ph(2,3,4-tri-F) | H | 128-131 | |
| 62 (3S, 4R) | Ph(4-CF$_3$) | Ph(3-Cl, 2-F) | H | 86-89 | |
| 63 (3R, 4S) | Ph(4-CF$_3$) | Ph(3-Cl, 2-F) | H | 123-127 | |

[(1)]Substituents in the 3- and 4- positions of the piperidinone ring, i.e. C(=O)N(Q$^2$)(H) and Q$^1$, respectivaly, are predominantely in the trans configuration.
*See Synthesis Example for $^1$H NMR data.

BIOLOGICAL EXAMPLES OF THE INVENTION

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), crabgrass, large (large crabgrass, *Digitaria sanguinalis*), foxtail, giant (giant foxtail, *Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 500 g ai/ha | Compounds | | | | | | | | | | | | | |
|---|---|---|---|---|---|---|---|---|---|---|---|---|---|---|
| Post emergence | 1 | 2 | 3 | 4 | 5 | 6 | 7 | 8 | 9 | 10 | 11 | 12 | 13 | 14 |
| Barnyardgrass | 50 | 0 | 0 | 20 | 30 | 50 | 0 | 0 | 90 | 90 | 90 | 60 | 90 | 90 |
| Blackgrass | — | — | — | — | — | — | 0 | 0 | — | — | 50 | 0 | 0 | 0 |
| Corn | 0 | 0 | 0 | 0 | 0 | 0 | 0 | 0 | 80 | 0 | 40 | 0 | 0 | 0 |
| Crabgrass, Large | 70 | 10 | 0 | 70 | 0 | 80 | — | — | 90 | 80 | — | — | — | — |
| Foxtail, Giant | 0 | 0 | 0 | 0 | 0 | 70 | 0 | 0 | 90 | 70 | 90 | 60 | 90 | 90 |
| *Galium* | — | — | — | — | — | — | 0 | 0 | — | — | 60 | 0 | 0 | 0 |
| *Kochia* | — | — | — | — | — | — | 0 | 0 | — | — | 50 | 0 | 0 | 0 |
| Morningglory | 0 | 0 | 0 | 0 | 0 | 0 | — | — | 40 | 0 | — | — | — | — |
| Pigweed | 0 | 0 | 0 | 0 | 0 | 30 | 0 | 0 | 0 | 0 | 30 | 0 | 0 | 0 |
| Ragweed | — | — | — | — | — | — | 0 | 0 | — | — | 20 | 0 | 0 | 0 |
| Ryegrass, Italian | — | — | — | — | — | — | 0 | 0 | — | — | 30 | 0 | 0 | 0 |
| Velvetleaf | 0 | 0 | 0 | 0 | 0 | 0 | — | — | 0 | 0 | — | — | — | — |
| Wheat | 0 | 0 | 0 | 0 | 0 | 0 | 0 | 0 | 40 | 0 | 50 | 0 | 0 | 0 |

| 500 g ai/ha | Compounds | | | | | | | | | | | | | |
|---|---|---|---|---|---|---|---|---|---|---|---|---|---|---|
| Postemergence | 15 | 16 | 17 | 19 | 20 | 21 | 22 | 23 | 24 | 25 | 26 | 27 | 28 | 29 |
| Barnyardgrass | 70 | 90 | 80 | 80 | 80 | 90 | 90 | 70 | 80 | 80 | 80 | 60 | 80 | 30 |
| Blackgrass | 50 | 60 | 30 | 50 | 20 | 80 | 60 | 10 | 30 | 80 | 40 | 0 | 20 | 0 |
| Corn | 0 | 30 | 0 | 50 | 20 | 80 | 60 | 20 | 30 | 70 | 40 | 0 | 60 | 0 |
| Crabgrass, Large | — | — | — | — | — | — | — | — | — | — | — | — | — | — |
| Foxtail, Giant | 80 | 80 | 80 | 80 | 80 | 80 | 90 | 60 | 80 | 80 | 90 | 70 | 90 | 0 |
| *Galium* | 70 | 20 | 20 | 20 | 0 | 20 | 70 | 20 | 0 | 30 | 0 | 0 | 0 | 0 |
| *Kochia* | 60 | 20 | 20 | 20 | 0 | 0 | 60 | 50 | 0 | 0 | 0 | 0 | 0 | 0 |
| Morningglory | — | — | — | — | — | — | — | — | — | — | — | — | — | — |
| Pigweed | 0 | 0 | 0 | 0 | 0 | 20 | 50 | 0 | 0 | 0 | 0 | 0 | 0 | 0 |
| Ragweed | 40 | 0 | 0 | 0 | 0 | 0 | 50 | 0 | 0 | 0 | 0 | 0 | 0 | 0 |
| Ryegrass, Italian | 0 | 20 | 20 | 20 | 20 | 40 | 70 | 20 | 20 | 40 | 20 | 0 | 0 | 0 |
| Velvetleaf | — | — | — | — | — | — | — | — | — | — | — | — | — | — |
| Wheat | 0 | 30 | 20 | 30 | 0 | 60 | 60 | 20 | 30 | 60 | 20 | 0 | 20 | 0 |

| 500 g ai/ha | Compounds | | | | | | | | | | | | | |
|---|---|---|---|---|---|---|---|---|---|---|---|---|---|---|
| Postemergence | 30 | 31 | 32 | 33 | 34 | 36 | 37 | 38 | 39 | 42 | 43 | 44 | 45 | 46 |
| Barnyardgrass | 80 | 80 | 70 | 90 | 90 | 90 | 80 | 70 | 80 | 90 | 0 | 80 | 60 | 90 |
| Blackgrass | 80 | 40 | 0 | 0 | 0 | 60 | 0 | 0 | 60 | 70 | 0 | 20 | 20 | 40 |
| Corn | 70 | 0 | 30 | 0 | 0 | 0 | 0 | 0 | 50 | 60 | 0 | 0 | 0 | 50 |
| Crabgrass, Large | — | — | — | — | — | — | — | — | — | — | — | — | — | — |
| Foxtail, Giant | 80 | 80 | 40 | 90 | 80 | 90 | 70 | 60 | 90 | 90 | 0 | 80 | 50 | 80 |
| *Galium* | 0 | 0 | 0 | 0 | 0 | 30 | 0 | 0 | 0 | 0 | 0 | 10 | 0 | 0 |
| *Kochia* | 0 | 0 | 20 | 0 | 0 | 0 | 0 | 0 | 0 | 30 | 0 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 20 | 0 | 20 | 0 | 0 | 20 | 20 | 0 | 50 | 50 | 0 | 20 | 0 | 0 |
| Velvetleaf | — | — | — | — | — | — | — | — | — | — | — | — | — | — |
| Wheat | 60 | 0 | 0 | 0 | 0 | 0 | 0 | 0 | 30 | 60 | 0 | 0 | 0 | 50 |

| 500 g ai/ha | Compounds | | | | | | | | |
|---|---|---|---|---|---|---|---|---|---|
| Postemergence | 47 | 48 | 49 | 50 | 51 | 52 | 53 | 55 | 57 |
| Barnyardgrass | 90 | 80 | 90 | 0 | 0 | 90 | 0 | 0 | 70 |
| Blackgrass | 0 | 0 | 50 | 0 | 0 | 0 | 20 | 0 | 0 |
| Corn | 0 | 0 | 50 | 0 | 0 | 10 | 20 | 0 | 0 |
| Crabgrass, Large | — | — | — | — | — | — | — | — | — |
| Foxtail, Giant | 80 | 30 | 80 | 0 | 0 | 80 | 20 | 0 | 60 |
| *Galium* | 0 | 0 | 0 | 0 | 0 | 50 | 0 | 0 | 0 |
| *Kochia* | 0 | 0 | 0 | 0 | 0 | 20 | 0 | 0 | 0 |
| Morningglory | — | — | — | — | — | — | — | — | — |
| Pigweed | 0 | 0 | 0 | 0 | 0 | 0 | 0 | 0 | 0 |
| Ragweed | 0 | 0 | 0 | 0 | 0 | 0 | 0 | 0 | 0 |
| Ryegrass, Italian | 20 | 0 | 0 | 0 | 0 | 20 | 0 | 0 | 0 |
| Velvetleaf | — | — | — | — | — | — | — | — | — |
| Wheat | 30 | 0 | 30 | 0 | 0 | 20 | 20 | 0 | 0 |

| 125 g ai/ha | Compounds | | | | | | | | | | | | | |
|---|---|---|---|---|---|---|---|---|---|---|---|---|---|---|
| Postemergence | 1 | 2 | 3 | 4 | 5 | 6 | 7 | 8 | 9 | 10 | 11 | 12 | 13 | 14 |
| Barnyardgrass | 0 | 0 | 0 | 0 | 0 | 0 | 0 | 0 | 80 | 80 | 70 | 20 | 30 | 20 |
| Blackgrass | — | — | — | — | — | — | 0 | 0 | — | — | 20 | 0 | 0 | 0 |
| Corn | 0 | 0 | 0 | 0 | 0 | 0 | 0 | 0 | 40 | 0 | 0 | 0 | 0 | 0 |
| Crabgrass, Large | 30 | 0 | 0 | 40 | 0 | 50 | — | — | 80 | 60 | — | — | — | — |

TABLE A-continued

| | | | | | | | | | | | | | | |
|---|---|---|---|---|---|---|---|---|---|---|---|---|---|---|
| Foxtail, Giant | 0 | 0 | 0 | 0 | 0 | 30 | 0 | 0 | 80 | 40 | 80 | 20 | 30 | 30 |
| *Galium* | — | — | — | — | — | — | 0 | 0 | — | — | 40 | 0 | 0 | 0 |
| *Kochia* | — | — | — | — | — | — | 0 | 0 | — | — | 20 | 0 | 0 | 0 |
| Morningglory | 0 | 0 | 0 | 0 | 0 | 0 | — | — | 0 | 0 | — | — | — | — |
| Pigweed | 0 | 0 | 0 | 0 | 0 | 0 | 0 | 0 | 0 | 0 | 0 | 0 | 0 | 0 |
| Ragweed | — | — | — | — | — | — | 0 | 0 | — | — | 0 | 0 | 0 | 0 |
| Ryegrass, Italian | — | — | — | — | — | — | 0 | 0 | — | — | 0 | 0 | 0 | 0 |
| Velvetleaf | 0 | 0 | 0 | 0 | 0 | 0 | — | — | 0 | 0 | — | — | — | — |
| Wheat | 0 | 0 | 0 | 0 | 0 | 0 | 0 | 0 | 20 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 15 | 16 | 17 | 19 | 20 | 21 | 22 | 23 | 24 | 25 | 26 | 27 | 28 | 29 |
| Barnyardgrass | 60 | 70 | 80 | 60 | 40 | 90 | 80 | 20 | 50 | 80 | 30 | 50 | 60 | 0 |
| Blackgrass | 20 | 40 | 30 | 40 | 0 | 60 | 50 | 0 | 0 | 60 | 0 | 0 | 0 | 0 |
| Corn | 0 | 0 | 0 | 0 | 0 | 50 | 0 | 0 | 20 | 20 | 20 | 0 | 30 | 0 |
| Crabgrass, Large | — | — | — | — | — | — | — | — | — | — | — | — | — | — |
| Foxtail, Giant | 70 | 80 | 80 | 70 | 40 | 80 | 90 | 20 | 50 | 80 | 30 | 40 | 70 | 0 |
| *Galium* | 30 | 20 | 20 | 20 | 0 | 0 | 50 | 0 | 0 | 30 | 0 | 0 | 0 | 0 |
| *Kochia* | 10 | 0 | 0 | 0 | 0 | 0 | 40 | 20 | 0 | 0 | 0 | 0 | 0 | 0 |
| Morningglory | — | — | — | — | — | — | — | — | — | — | — | — | — | — |
| Pigweed | 0 | 0 | 0 | 0 | 0 | 0 | 40 | 0 | 0 | 0 | 0 | 0 | 0 | 0 |
| Ragweed | 0 | 0 | 0 | 0 | 0 | 0 | 50 | 0 | 0 | 0 | 0 | 0 | 0 | 0 |
| Ryegrass, Italian | 0 | 0 | 0 | 0 | 0 | 30 | 40 | 0 | 0 | 30 | 20 | 0 | 0 | 0 |
| Velvetleaf | — | — | — | — | — | — | — | — | — | — | — | — | — | — |
| Wheat | 0 | 20 | 20 | 0 | 0 | 0 | 0 | 0 | 20 | 40 | 0 | 0 | 0 | 0 |

| 125 g ai/ha | Compounds | | | | | | | | | | | | | |
|---|---|---|---|---|---|---|---|---|---|---|---|---|---|---|
| Postemergence | 30 | 31 | 32 | 33 | 34 | 36 | 37 | 38 | 39 | 42 | 43 | 44 | 45 | 46 |
| Barnyardgrass | 80 | 60 | 60 | 60 | 40 | 80 | 60 | 50 | 80 | 80 | 0 | 20 | 0 | 60 |
| Blackgrass | 70 | 20 | 0 | 0 | 0 | 0 | 0 | 0 | 0 | 0 | 40 | 0 | 0 | 0 |
| Corn | 30 | 0 | 0 | 0 | 0 | 0 | 0 | 0 | 0 | 10 | 0 | 0 | 0 | 0 |
| Crabgrass, Large | — | — | — | — | — | — | — | — | — | — | — | — | — | — |
| Foxtail, Giant | 80 | 70 | 40 | 50 | 40 | 90 | 20 | 0 | 70 | 90 | 0 | 30 | 0 | 20 |
| *Galium* | 0 | 0 | 0 | 0 | 0 | 0 | 0 | 0 | 0 | 0 | 0 | 0 | 0 | 0 |
| *Kochia* | 0 | 0 | 0 | 0 | 0 | 0 | 0 | 0 | 0 | 0 | 0 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 40 | 0 | 0 | 0 | 0 |
| Velvetleaf | — | — | — | — | — | — | — | — | — | — | — | — | — | — |
| Wheat | 30 | 0 | 0 | 0 | 0 | 0 | 0 | 0 | 0 | 0 | 0 | 0 | 0 | 0 |

| 125 g ai/ha | Compounds | | | | | | | | |
|---|---|---|---|---|---|---|---|---|---|
| Postemergence | 47 | 48 | 49 | 50 | 51 | 52 | 53 | 55 | 57 |
| Barnyardgrass | 50 | 30 | 80 | 0 | 0 | 70 | 0 | 0 | 0 |
| Blackgrass | 0 | 0 | 0 | 0 | 0 | 0 | 0 | 0 | 0 |
| Corn | 0 | 0 | 0 | 0 | 0 | 0 | 0 | 0 | 0 |
| Crabgrass, Large | — | — | — | — | — | — | — | — | — |
| Foxtail, Giant | 70 | 0 | 80 | 0 | 0 | 80 | 0 | 0 | 0 |
| *Galium* | 0 | 0 | 0 | 0 | 0 | 0 | 0 | 0 | 0 |
| *Kochia* | 0 | 0 | 0 | 0 | 0 | 0 | 0 | 0 | 0 |
| Morningglory | — | — | — | — | — | — | — | — | — |
| Pigweed | 0 | 0 | 0 | 0 | 0 | 0 | 0 | 0 | 0 |
| Ragweed | 0 | 0 | 0 | 0 | 0 | 0 | 0 | 0 | 0 |
| Ryegrass, Italian | 0 | 0 | 0 | 0 | 0 | 0 | 0 | 0 | 0 |
| Velvetleaf | — | — | — | — | — | — | — | — | — |
| Wheat | 0 | 0 | 0 | 0 | 0 | 0 | 0 | 0 | 0 |

| 500 g ai/ha | Compounds | | | | | | | | | | | | | |
|---|---|---|---|---|---|---|---|---|---|---|---|---|---|---|
| Preemergence | 1 | 2 | 3 | 4 | 5 | 6 | 7 | 8 | 9 | 10 | 11 | 12 | 13 | 14 |
| Barnyardgrass | 70 | 20 | 0 | 50 | 30 | 80 | 0 | 0 | 90 | 90 | 90 | 70 | 70 | 90 |
| Corn | 0 | 0 | 0 | 0 | 0 | 0 | — | — | 70 | 0 | — | — | — | — |
| Crabgrass, Large | 90 | 90 | 30 | 90 | 90 | 90 | — | — | 100 | 100 | — | — | — | — |
| Foxtail, Giant | 90 | 70 | 0 | 70 | 50 | 90 | 0 | 0 | 90 | 90 | 90 | 70 | 90 | 90 |
| *Kochia* | — | — | — | — | — | — | 0 | 0 | — | — | 60 | 0 | 40 | 20 |
| Morningglory | 0 | 0 | 0 | 0 | 0 | 0 | — | — | 0 | 0 | — | — | — | — |
| Pigweed | 0 | 0 | 0 | 0 | 0 | 0 | — | — | 0 | 0 | 40 | 0 | 0 | 0 |
| Ragweed | — | — | — | — | — | — | 0 | 0 | — | — | 80 | 0 | 0 | 0 |
| Ryegrass, Italian | — | — | — | — | — | — | 0 | 0 | — | — | 0 | 0 | 0 | 0 |
| Velvetleaf | 0 | 0 | 0 | 0 | 0 | 0 | — | — | 0 | 0 | — | — | — | — |
| Wheat | 0 | 0 | 20 | 0 | 0 | 0 | — | — | 50 | 0 | — | — | — | — |

TABLE A-continued

| 500 g ai/ha | Compounds | | | | | | | | | | | | | |
|---|---|---|---|---|---|---|---|---|---|---|---|---|---|---|
| Preemergence | 15 | 16 | 17 | 19 | 20 | 21 | 22 | 23 | 24 | 25 | 26 | 27 | 28 | 29 |
| Barnyardgrass | 80 | 90 | 80 | 80 | 90 | 90 | 90 | 70 | 80 | 90 | 90 | 90 | 90 | 20 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 80 | 80 | 90 | 90 | 90 | 90 | 20 |
| *Kochia* | 0 | 50 | 30 | 20 | 0 | 0 | 80 | 40 | 0 | 0 | 0 | 0 | 20 | 0 |
| Morningglory | — | — | — | — | — | — | — | — | — | — | — | — | — | — |
| Pigweed | 0 | 0 | 0 | 0 | 0 | 0 | 50 | 0 | 0 | 0 | 0 | 0 | 20 | 0 |
| Ragweed | 80 | 0 | 0 | 20 | 0 | 0 | 80 | 60 | 0 | 0 | 0 | 0 | 0 | 0 |
| Ryegrass, Italian | 0 | 40 | 40 | 30 | 0 | 60 | 60 | 20 | 0 | 50 | 50 | 0 | 40 | 0 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 30 | 31 | 32 | 33 | 34 | 36 | 37 | 38 | 39 | 42 | 43 | 44 | 45 | 46 |
| Barnyardgrass | 90 | 80 | 90 | 90 | 90 | 90 | 70 | 80 | 90 | 90 | 0 | 90 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 80 | 90 | 90 | 0 | 90 | 80 | 90 |
| *Kochia* | 0 | 0 | 20 | 30 | 30 | 0 | 0 | 0 | 0 | 0 | 0 | 0 | 0 | 0 |
| Morningglory | — | — | — | — | — | — | — | — | — | — | — | — | — | — |
| Pigweed | 0 | 0 | 0 | 0 | 30 | 0 | 0 | 0 | 10 | 10 | 0 | 0 | 0 | 0 |
| Ragweed | 0 | 0 | 0 | 0 | 30 | 0 | 0 | 0 | 0 | 0 | 0 | 30 | 0 | 0 |
| Ryegrass, Italian | 50 | 0 | 30 | 0 | 0 | 30 | 0 | 0 | 70 | 60 | 0 | 0 | 0 | 20 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | |
|---|---|---|---|---|---|---|---|---|---|
| Preemergence | 47 | 48 | 49 | 50 | 51 | 52 | 53 | 55 | 57 |
| Barnyardgrass | 90 | 90 | 90 | 0 | 0 | 90 | 80 | 0 | 70 |
| Corn | — | — | — | — | — | — | — | — | — |
| Crabgrass, Large | — | — | — | — | — | — | — | — | — |
| Foxtail, Giant | 90 | 90 | 90 | 40 | 0 | 90 | 90 | 0 | 90 |
| *Kochia* | 0 | 0 | 0 | 0 | 0 | 20 | 0 | 0 | 0 |
| Morningglory | — | — | — | — | — | — | — | — | — |
| Pigweed | 0 | 0 | 0 | 0 | 0 | 80 | 50 | 0 | 0 |
| Ragweed | 0 | 0 | 0 | 0 | 0 | 30 | 0 | 0 | 0 |
| Ryegrass, Italian | 40 | 0 | 60 | 0 | 0 | 30 | 0 | 0 | 0 |
| Velvetleaf | — | — | — | — | — | — | — | — | — |
| Wheat | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 1 | 2 | 3 | 4 | 5 | 6 | 7 | 8 | 9 | 10 | 11 | 12 | 13 | 14 |
| Barnyardgrass | 0 | 0 | 0 | 0 | 0 | 60 | 0 | 0 | 90 | 60 | 60 | 20 | 40 | 50 |
| Corn | 0 | 0 | 0 | 0 | 0 | 0 | — | — | 20 | 0 | — | — | — | — |
| Crabgrass, Large | 80 | 70 | 0 | 90 | 60 | 90 | — | — | 90 | 90 | — | — | — | — |
| Foxtail, Giant | 30 | 10 | 0 | 10 | 30 | 60 | 0 | 0 | 90 | 90 | 70 | 20 | 70 | 30 |
| *Kochia* | — | — | — | — | — | 0 | 0 | — | — | 0 | 0 | 0 | 0 | 0 |
| Morningglory | 0 | 0 | 0 | 0 | 0 | 0 | — | — | 0 | 0 | — | — | — | — |
| Pigweed | 0 | 0 | 0 | 0 | 0 | 0 | 0 | 0 | 0 | 0 | 0 | 0 | 0 | 0 |
| Ragweed | — | — | — | — | — | — | 0 | 0 | — | — | 40 | 0 | 0 | 0 |
| Ryegrass, Italian | — | — | — | — | — | — | 0 | 0 | — | — | 0 | 0 | 0 | 0 |
| Velvetleaf | 0 | 0 | 0 | 0 | 0 | 0 | — | — | 0 | 0 | — | — | — | — |
| Wheat | 0 | 0 | 0 | 0 | 0 | 0 | — | — | 20 | 0 | — | — | — | — |

| 125 g ai/ha | Compounds | | | | | | | | | | | | | |
|---|---|---|---|---|---|---|---|---|---|---|---|---|---|---|
| Preemergence | 15 | 16 | 17 | 19 | 20 | 21 | 22 | 23 | 24 | 25 | 26 | 27 | 28 | 29 |
| Barnyardgrass | 60 | 70 | 50 | 70 | 50 | 90 | 90 | 30 | 50 | 90 | 30 | 60 | 90 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 80 | 90 | 80 | 80 | 60 | 90 | 90 | 30 | 70 | 90 | 60 | 80 | 90 | 0 |
| *Kochia* | 0 | 30 | 30 | 0 | 0 | 0 | 70 | 0 | 0 | 0 | 0 | 0 | 20 | 0 |
| Morningglory | — | — | — | — | — | — | — | — | — | — | — | — | — | — |
| Pigweed | 0 | 0 | 0 | 0 | 0 | 0 | 20 | 0 | 0 | 0 | 0 | 0 | 0 | 0 |
| Ragweed | 0 | 0 | 0 | 0 | 0 | 0 | 60 | 0 | 0 | 0 | 0 | 0 | 0 | 0 |
| Ryegrass, Italian | 0 | 20 | 20 | 20 | 0 | 0 | 20 | 0 | 0 | 0 | 0 | 0 | 20 | 0 |
| Velvetleaf | — | — | — | — | — | — | — | — | — | — | — | — | — | — |
| Wheat | — | — | — | — | — | — | — | — | — | — | — | — | — | — |

TABLE A-continued

| 125 g ai/ha | Compounds | | | | | | | | | | | | | |
|---|---|---|---|---|---|---|---|---|---|---|---|---|---|---|
| Preemergence | 30 | 31 | 32 | 33 | 34 | 36 | 37 | 38 | 39 | 42 | 43 | 44 | 45 | 46 |
| Barnyardgrass | 90 | 70 | 20 | 50 | 40 | 90 | 40 | 30 | 80 | 90 | 0 | 60 | 20 | 50 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 70 | 70 | 70 | 50 | 90 | 70 | 50 | 90 | 90 | 0 | 80 | 40 | 90 |
| Kochia | 0 | 0 | 0 | 0 | 0 | 0 | 0 | 0 | 0 | 0 | 0 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 20 | 0 | 0 | 0 | 0 | 0 | 0 | 0 | 30 | 40 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | |
|---|---|---|---|---|---|---|---|---|---|
| Preemergence | 47 | 48 | 49 | 50 | 51 | 52 | 53 | 55 | 57 |
| Barnyardgrass | 70 | 40 | 80 | 0 | 0 | 90 | 0 | 0 | 30 |
| Corn | — | — | — | — | — | — | — | — | — |
| Crabgrass, Large | — | — | — | — | — | — | — | — | — |
| Foxtail, Giant | 80 | 70 | 90 | 0 | 0 | 90 | 0 | 0 | 60 |
| Kochia | 0 | 0 | 0 | 0 | 0 | 0 | 0 | 0 | 0 |
| Morningglory | — | — | — | — | — | — | — | — | — |
| Pigweed | 0 | 0 | 0 | 0 | 0 | 30 | 0 | 0 | 0 |
| Ragweed | 0 | 0 | 0 | 0 | 0 | 20 | 0 | 0 | 0 |
| Ryegrass, Italian | 0 | 0 | 0 | 0 | 0 | 20 | 0 | 0 | 0 |
| Velvetleaf | — | — | — | — | — | — | — | — | — |
| Wheat | — | — | — | — | — | — | — | — | — |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At the time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| 1000 g ai/ha | Compounds | | |
|---|---|---|---|
| Flood | 7 | 13 | 14 |
| Barnyardgrass | 0 | 40 | 30 |
| Ducksalad | 0 | 100 | 100 |
| Rice | 0 | 0 | 0 |
| Sedge, Umbrella | 0 | 0 | 0 |

| 500 g ai/ha | Compounds | | | | | | | | | | | | | |
|---|---|---|---|---|---|---|---|---|---|---|---|---|---|---|
| Flood | 15 | 16 | 17 | 19 | 26 | 27 | 28 | 31 | 32 | 33 | 34 | 44 | 45 | 46 |
| Barnyardgrass | 40 | 0 | 35 | 60 | 40 | 0 | 100 | 95 | 0 | 20 | 0 | 60 | 0 | 65 |
| Ducksalad | 60 | 0 | 40 | 60 | 50 | 0 | 85 | 0 | 40 | 80 | 40 | 85 | 50 | 100 |
| Rice | 0 | 0 | 0 | 0 | 0 | 0 | 15 | 10 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1 | 2 | 3 | 4 | 5 | 6 | 9 | 10 | 13 | 14 | 20 | 21 | 22 | 23 |
| Barnyardgrass | 0 | 0 | 0 | 0 | 0 | 0 | 75 | 0 | 0 | 30 | 0 | 75 | 65 | 0 |
| Ducksalad | 0 | 0 | 0 | 0 | 0 | 60 | 90 | 40 | 70 | 80 | 0 | 100 | 100 | 0 |
| Rice | 0 | 0 | 0 | 0 | 0 | 0 | 0 | 10 | 0 | 0 | 0 | 10 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 24 | 25 | 29 | 30 | 36 | 37 | 38 | 39 | 42 | 43 | 47 | 48 | 49 | 50 |

TABLE B-continued

| | | | | | | | | | | | | | | | |
|---|---|---|---|---|---|---|---|---|---|---|---|---|---|---|---|
| Barnyardgrass | 0 | 60 | 0 | 50 | 60 | 35 | 35 | 65 | 75 | 0 | 0 | 20 | 70 | 0 | |
| Ducksalad | 0 | 45 | 0 | 50 | 90 | 90 | 85 | 100 | 95 | 0 | 50 | 60 | 100 | 0 | |
| Rice | 0 | 0 | 0 | 20 | 0 | 0 | 0 | 0 | 0 | 0 | 0 | 15 | 0 | 0 | |
| Sedge, Umbrella | 0 | 0 | 0 | 0 | 0 | 0 | 0 | 0 | 0 | 0 | 0 | 0 | 0 | 0 | |

| 250 g ai/ha | Compounds | | | | |
|---|---|---|---|---|---|
| Flood | 51 | 52 | 53 | 55 | 57 |
| Barnyardgrass | 0 | 30 | 0 | 0 | 0 |
| Ducksalad | 0 | 100 | 0 | 0 | 40 |
| Rice | 0 | 0 | 0 | 0 | 0 |
| Sedge, Umbrella | 0 | 0 | 0 | 0 | 0 |

Test C

Seeds of plant species selected from blackgrass (*Alopecurus myosuroides*), ryegrass, Italian (Italian ryegrass, *Lolium multiflorum*), wheat (winter wheat, *Triticum aestivum*), galium (catchweed bedstraw, *Galium aparine*), corn (*Zea mays*), crabgrass, large (large crabgrass, *Digitaria sanguinalis*), foxtail, giant (giant foxtail, *Setaria faberii*), johnsongrass (*Sorghum halepense*), lambsquarters (*Chenopodium album*), morningglory (*Ipomoea coccinea*), yellow (yellow nutsedge, *Cyperus esculentus*), pigweed (*Amaranthus retroflexus*), ragweed (common ragweed, *Ambrosia elatior*), soybean (*Glycine max*), barnyardgrass (*Echinochloa crus-galli*), oilseed rape (*Brassica napus*), waterhemp (common waterhemp, *Amaranthus rudis*), and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also chickweed (common chickweed, *Stellaria media*), kochia (*Kochia scoparia*), and oat, wild (wild oat, *Avena fatua*) were planted in pots containing Sunshine Redi-Earth® planting medium comprising spaghnum peat moss, vermiculite, starter nutrients and dolomitic limestone and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

Plant species in the flooded paddy test consisted of rice (*Oryza sativa*), sedge, umbrella (small-flower umbrella sedge, *Cyperus difformis*), ducksalad (*Heteranthera limosa*), and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

TABLE C

| | Compounds | |
|---|---|---|
| | 9 | 17 |
| 250 g ai/ha Postemergence | | |
| Barnyardgrass | 85 | 50 |
| Blackgrass | 0 | 0 |
| Chickweed | 5 | 5 |
| Corn | 0 | 0 |
| Crabgrass, Large | 75 | 55 |
| Foxtail, Giant | 85 | 5 |
| *Galium* | 40 | 0 |
| Johnsongrass | 5 | 0 |
| *Kochia* | 0 | 0 |
| Lambsquarters | 0 | 80 |
| Morningglory | 40 | 5 |
| Nutsedge, Yellow | 0 | 0 |
| Oat, Wild | 0 | 0 |
| Oilseed Rape | 5 | 0 |
| Pigweed | 5 | 5 |
| Ragweed | 5 | 0 |
| Ryegrass, Italian | 0 | 0 |
| Soybean | 10 | 0 |
| Velvetleaf | 0 | 0 |
| Waterhemp | 5 | 0 |
| Wheat | 0 | 0 |
| 125 g ai/ha Postemergence | | |
| Barnyardgrass | 60 | 5 |
| Blackgrass | 0 | 0 |
| Chickweed | 0 | 0 |
| Corn | 0 | 0 |
| Crabgrass, Large | 75 | 20 |
| Foxtail, Giant | 35 | 5 |
| *Galium* | 0 | 0 |
| Johnsongrass | 0 | 0 |
| *Kochia* | 0 | 0 |
| Lambsquarters | 5 | — |
| Morningglory | 30 | 0 |
| Nutsedge, Yellow | 0 | 0 |
| Oat, Wild | 0 | 0 |
| Oilseed Rape | 0 | 0 |
| Pigweed | 5 | 0 |
| Ragweed | 0 | 0 |
| Ryegrass, Italian | 0 | 0 |
| Soybean | 0 | 0 |
| Velvetleaf | 0 | 0 |
| Waterhemp | 0 | 0 |
| Wheat | 0 | 0 |
| 62 g ai/ha Postemergence | | |
| Barnyardgrass | 5 | 0 |
| Blackgrass | 0 | 0 |
| Chickweed | 0 | 0 |
| Corn | 0 | 0 |
| Crabgrass, Large | 35 | 20 |
| Foxtail, Giant | 5 | 5 |

TABLE C-continued

| | Compounds | |
|---|---|---|
| | 9 | 28 |
| *Galium* | 0 | 0 |
| Johnsongrass | 0 | 0 |
| *Kochia* | 0 | 0 |
| Lambsquarters | 0 | 75 |
| Morningglory | 0 | 0 |
| Nutsedge, Yellow | 0 | 0 |
| Oat, Wild | 0 | 0 |
| Oilseed Rape | 0 | 0 |
| Pigweed | 0 | 0 |
| Ragweed | 0 | 0 |
| Ryegrass, Italian | 0 | 0 |
| Soybean | 0 | 10 |
| Velvetleaf | 0 | 0 |
| Waterhemp | 5 | 0 |
| Wheat | 0 | 0 |
| 31 g ai/ha Postemergence | | |
| Barnyardgrass | 0 | 0 |
| Blackgrass | 0 | 0 |
| Chickweed | 0 | 0 |
| Corn | 0 | 0 |
| Crabgrass, Large | 0 | 5 |
| Foxtail, Giant | 0 | 0 |
| *Galium* | 0 | 0 |
| Johnsongrass | 0 | 0 |
| *Kochia* | 0 | 0 |
| Lambsquarters | 0 | — |
| Morningglory | 0 | 0 |
| Nutsedge, Yellow | 0 | 0 |
| Oat, Wild | 0 | 0 |
| Oilseed Rape | 0 | 0 |
| Pigweed | 0 | 0 |
| Ragweed | 0 | 0 |
| Ryegrass, Italian | 0 | 0 |
| Soybean | 0 | 0 |
| Velvetleaf | 0 | 0 |
| Waterhemp | 0 | 0 |
| Wheat | 0 | 0 |

| | Compounds | |
|---|---|---|
| | 9 | 28 |
| 250 g ai/ha Preemergence | | |
| Barnyardgrass | 95 | 95 |
| Blackgrass | 90 | 90 |
| Corn | 90 | 55 |
| Crabgrass, Large | 98 | 90 |
| Foxtail, Giant | 98 | 95 |
| *Galium* | 75 | — |
| Johnsongrass | 55 | 10 |
| Lambsquarters | 0 | 15 |
| Morningglory | 45 | 30 |
| Nutsedge, Yellow | 0 | 50 |
| Oilseed Rape | 40 | 0 |
| Pigweed | 10 | — |
| Ragweed | 20 | 0 |
| Ryegrass, Italian | 80 | 35 |
| Soybean | 0 | 0 |
| Velvetleaf | 0 | 20 |
| Waterhemp | 0 | 60 |
| Wheat | 70 | 10 |
| 125 g ai/ha Preemergence | | |
| Barnyardgrass | 95 | 90 |
| Blackgrass | 80 | 70 |
| Corn | 75 | 30 |
| Crabgrass, Large | 98 | 90 |
| Foxtail, Giant | 95 | 95 |
| *Galium* | 0 | — |
| Johnsongrass | 35 | 0 |
| Lambsquarters | 0 | 5 |
| Morningglory | 5 | 5 |
| Nutsedge, Yellow | 0 | 10 |
| Oilseed Rape | 0 | 0 |
| Pigweed | 0 | 0 |
| Ragweed | 10 | 0 |
| Ryegrass, Italian | 30 | 0 |
| Soybean | 0 | 0 |
| Velvetleaf | 0 | 20 |
| Waterhemp | 20 | 0 |
| Wheat | 55 | 0 |
| 62 g ai/ha Preemergence | | |
| Barnyardgrass | 90 | 75 |
| Blackgrass | 40 | 40 |
| Corn | 0 | 0 |
| Crabgrass, Large | 95 | 85 |
| Foxtail, Giant | 95 | 85 |
| *Galium* | 0 | — |
| Johnsongrass | 0 | 0 |
| Lambsquarters | 0 | 5 |
| Morningglory | 20 | 5 |
| Nutsedge, Yellow | 0 | 0 |
| Oilseed Rape | 0 | 0 |
| Pigweed | 0 | — |
| Ragweed | 0 | 0 |
| Ryegrass, Italian | 50 | 0 |
| Soybean | 0 | 0 |
| Velvetleaf | 5 | 0 |
| Waterhemp | 0 | — |
| Wheat | 30 | 0 |
| 31 g ai/ha Preemergence | | |
| Barnyardgrass | 75 | 60 |
| Blackgrass | 50 | 35 |
| Corn | 0 | 0 |
| Crabgrass, Large | 95 | 80 |
| Foxtail, Giant | 90 | 60 |
| *Galium* | 0 | 0 |
| Johnsongrass | 0 | 0 |
| Lambsquarters | 0 | 5 |
| Morningglory | 0 | 5 |
| Nutsedge, Yellow | 0 | 0 |
| Oilseed Rape | 0 | 0 |
| Pigweed | 5 | — |
| Ragweed | 0 | 0 |
| Ryegrass, Italian | 30 | 0 |
| Soybean | 0 | 0 |
| Velvetleaf | 0 | 10 |
| Waterhemp | 15 | 0 |
| Wheat | 0 | 0 |

| 1000 g ai/ha | Compounds | | | |
|---|---|---|---|---|
| Flood | 9 | 10 | 11 | 12 |
| Barnyardgrass | 80 | 65 | 70 | 25 |
| Ducksalad | 98 | 85 | 100 | 100 |
| Rice | 10 | 10 | 0 | 0 |
| Sedge, Umbrella | 0 | 0 | 0 | 25 |

| 500 g ai/ha | Compounds | |
|---|---|---|
| Flood | 11 | 12 |
| Barnyardgrass | 50 | 20 |
| Ducksalad | 95 | 75 |
| Rice | 0 | 0 |
| Sedge, Umbrella | 0 | 10 |

| | Compounds | | | | |
|---|---|---|---|---|---|
| | 11 | 12 | 16 | 19 | 28 |
| 250 g ai/ha Flood | | | | | |
| Barnyardgrass | 20 | 15 | 0 | 0 | 75 |
| Ducksalad | 80 | 35 | 0 | 0 | 70 |

| | | | | | |
|---|---|---|---|---|---|
| Rice | 0 | 0 | 0 | 0 | 0 |
| Sedge, Umbrella | 0 | 0 | 0 | 0 | 0 |
| 125 g ai/ha Flood | | | | | |
| Barnyardgrass | 10 | 0 | 0 | 0 | 70 |
| Ducksalad | 30 | 0 | 0 | 0 | 60 |
| Rice | 0 | 0 | 0 | 0 | 0 |
| Sedge, Umbrella | 0 | 0 | 0 | 0 | 0 |

| | Compounds | | |
|---|---|---|---|
| | 16 | 19 | 28 |
| 62 g ai/ha Flood | | | |
| Barnyardgrass | 0 | 0 | 65 |
| Ducksalad | 0 | 0 | 50 |
| Rice | 0 | 0 | 0 |
| Sedge, Umbrella | 0 | 0 | 0 |
| 31 g ai/ha Flood | | | |
| Barnyardgrass | 0 | 0 | 60 |
| Ducksalad | 0 | 0 | 45 |
| Rice | 0 | 0 | 0 |
| Sedge, Umbrella | 0 | 0 | 0 |

What is claimed is:

1. A compound of Formula 1, N-oxides and salts thereof:

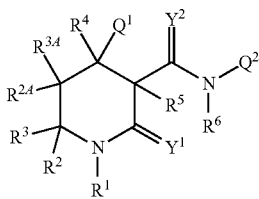

wherein
- $Q^1$ is a phenyl ring or a naphthalenyl ring system, each ring or ring system optionally substituted with up to 5 substituents independently selected from $R^7$; or a 4- to 7-membered heterocyclic ring or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members;
- $Q^2$ is a phenyl ring or a naphthalenyl ring system, each ring or ring system optionally substituted with up to 5 substituents independently selected from $R^{10}$; or a 4- to 7-membered heterocyclic ring or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members;
- $Y^1$ and $Y^2$ are each independently O, S or $NR^{12}$;
- $R^1$ is H, hydroxy, amino, $C_1$-$C_6$ alkyl, cyano, formyl, $C_3$-$C_8$ alkylcarbonylalkyl, —C($C_1$-$C_4$ alkyl)=N—O($C_1$-$C_4$ alkyl), —C(O)NH$_2$, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or arylcarbonyl, arylalkenylalkyl, arylcarbonylalkyl or —CPh=N—O($C_1$-$C_4$ alkyl), each optionally substituted on ring members with up to 5 substituents independently selected from $R^{13}$; or $G^1$;
- $R^2$ and $R^3$ are each independently H, halogen, hydroxy, $C_1$-$C_4$ alkyl, $C_1$-$C_4$ haloalkyl or $C_1$-$C_4$ alkoxy; or
- $R^2$ and $R^3$ are taken together with the carbon atom to which they are bonded to form a $C_3$-$C_7$ cycloalkyl ring;
- $R^{2A}$ and $R^{3A}$ are each independently H, halogen, hydroxy, $C_1$-$C_4$ alkyl, $C_1$-$C_4$ haloalkyl or $C_1$-$C_4$ alkoxy; or
- $R^{2A}$ and $R^{3A}$ are taken together with the carbon atom to which they are bonded to form a $C_3$-$C_7$ cycloalkyl ring or C=O;
- $R^4$ and $R^5$ are each independently H, halogen, hydroxy, $C_1$-$C_4$ alkoxy, $C_1$-$C_4$ haloalkyl or $C_1$-$C_4$ alkyl;
- $R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$; or
- $R^6$ and $Q^2$ are taken together with the nitrogen atom to which they are bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members;

each $R^7$ and $R^{10}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_3$-$C_8$ alkoxyalkoxyalkyl, $C_2$-$C_8$ haloalkoxyhaloalkoxy, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or $G^2$;

each $R^8$ is independently H, cyano, $C_2$-$C_3$ alkylcarbonyl or $C_2$-$C_3$ haloalkylcarbonyl;

each $R^9$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl, $C_2$-$C_6$ haloalkylcarbonyl, —(C=O)CH$_3$ or —(C=O)CF$_3$;

each $G^1$ is independently phenyl, phenylmethyl, pyridinylmethyl, phenylcarbonyl, phenoxy, phenylethynyl, phenylsulfonyl, p-methoxybenzyl or a 5- or 6-membered heteroaromatic ring, each optionally substituted on ring members with up to 5 substituents independently selected from $R^{13}$;

each $G^2$ is independently phenyl, phenylmethyl, pyridinylmethyl, phenylcarbonyl, phenoxy, phenylethynyl, phenylsulfonyl or a 5- or 6-membered heteroaromatic ring, each optionally substituted on ring members with up to 5 substituents independently selected from $R^{14}$;

each $R^{13}$ and $R^{14}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl; and each u and v are independently 0, 1 or 2 in each instance of $S(=O)_u(=NR^8)_v$, provided that the sum of u and v is 0, 1 or 2.

2. The compound of claim 1 wherein each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, $C_2$-$C_4$ alkylamino, $C_2$-$C_4$ dialkylamino, formylamino, $C_2$-$C_4$ alkylcarbonylamino, —SF$_5$, —SCN, $C_3$-$C_4$ trialkylsilyl, trimethylsilylmethyl or trimethylsilylmethoxy; and each $R^9$ and $R^{11}$ is independently $C_1$-$C_2$ alkyl.

3. The compound of claim 2 wherein $Y^1$ and $Y^2$ are each O;

$R^1$ is H or $C_1$-$C_6$ alkyl; and $R^2$, $R^3$, $R^{2A}$, $R^{3A}$, $R^4$, $R^5$ and $R^6$ are each H.

4. The compound of claim 3 wherein $R^1$ is H or Me.

5. The compound of claim 4 wherein $Q^1$ is a phenyl ring substituted with 1 to 3 substituents independently selected from $R^7$; and $Q^2$ is a phenyl ring substituted with 1 to 3 substituents independently selected from $R^{10}$.

6. The compound of claim 5 wherein each $R^7$ is independently halogen, cyano, $C_1$-$C_2$ alkyl, $C_1$-$C_3$ haloalkyl or $C_1$-$C_3$ alkylsulfonyl; and each $R^{10}$ is independently halogen, cyano, nitro, $C_1$-$C_2$ alkyl, $C_1$-$C_3$ haloalkyl or $C_1$-$C_3$ alkylsulfonyl.

7. The compound of claim 6 wherein $Q^1$ is a phenyl ring substituted with 1 substituent selected from $R^7$ at a meta position or the para position or substituted with 2 substituents independently selected from $R^7$ wherein one substituent is at a meta position and the other substituent is at the para position; and $Q^2$ is a phenyl ring substituted with 1 substituent selected from $R^{10}$ at an ortho position or substituted with 2 substituents independently selected from $R^{10}$ wherein one substituent is at an ortho position and the other substituent is at the adjacent meta position.

8. The compound of claim 7 wherein each $R^7$ is independently F or CF$_3$; and each $R^{10}$ is F.

9. The compound of claim 1 selected from the group consisting of

N-(2,3-difluorophenyl)-2-oxo-4-[3-(trifluoromethyl)phenyl]-3-piperidinecarboxamide;

2-oxo-N-[2-(trifluoromethyl)phenyl]-4-[3-(trifluoromethyl)phenyl]-3-piperidinecarboxamide; and
N-(2,3-difluorophenyl)-2-oxo-4-[4-(trifluoromethyl)phenyl]-3-piperidinecarboxamide.

10. The compound of claim 1 selected from the group consisting of
N-(2,3-difluorophenyl)-2-oxo-4-[3-(trifluoromethyl)phenyl]-3-piperidinecarboxamide;
2-oxo-N-[2-(trifluoromethyl)phenyl]-4-[3-(trifluoromethyl)phenyl]-3-piperidinecarboxamide;
N-(2,3-difluorophenyl)-2-oxo-4-[4-(trifluoromethyl)phenyl]-3-piperidinecarboxamide;
(3S,4S)—N-(2,3-difluorophenyl)-4-(4-fluorophenyl)-1-methyl-2-oxo-3-piperidinecarboxamide;
4-[3-(difluoromethyl)phenyl]-N-(2,3-difluorophenyl)-2-oxo-3-piperidinecarboxamide;
(3R,4S)-4-(3-chlorophenyl)-N-(2,3-difluorophenyl)-2-oxo-3-piperidinecarboxamide;
4-(3-chlorophenyl)-N-(2,3-difluorophenyl)-2-oxo-3-piperidinecarboxamide;
2-oxo-4-[3-(trifluoromethyl)phenyl]-N-(2,3,4-trifluorophenyl)-3-piperidinecarboxamide;
(3R,4S)—N-(3-chloro-2-fluorophenyl)-2-oxo-4-[3-(trifluoromethyl)phenyl]-3-piperidinecarboxamide;
(3R,4S)—N-(2,3-difluorophenyl)-2-oxo-4-[4-(trifluoromethyl)phenyl]-3-piperidinecarboxamide; and
(3R,4S)—N-(2,3-difluorophenyl)-2-oxo-4-[3-(trifluoromethyl)phenyl]-3-piperidinecarboxamide.

11. A herbicidal composition comprising a compound of claim 1 and at least one component selected from the group consisting of surfactants, solid diluents and liquid diluents.

12. The herbicidal composition of claim 11 further comprising at least one additional active ingredient selected from the group consisting of other herbicides and herbicide safeners.

13. A herbicidal mixture comprising (a) a compound of claim 1, and (b) at least one additional active ingredient selected from the group consisting of (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides selected from the group consisting of mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b 1) through (b16).

14. A method for controlling the growth of undesired vegetation comprising contacting the vegetation or its environment with a herbicidally effective amount of a compound of claim 1.

15. A compound of the following Formula

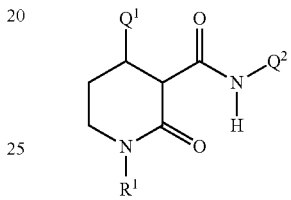

wherein $R^1$ is Me; $Q^2$ is Ph(2-F); and $Q^1$ is Ph(3-CF$_3$).

16. A compound of the following Formula

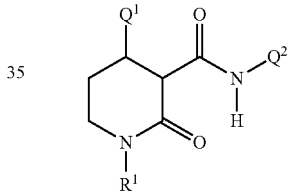

wherein $R^1$ is Me; $Q^2$ is Ph(2,3,4-tri-F); and $Q^1$ is Ph(4-CF$_3$).

* * * * *